United States Patent
McCafferty

(10) Patent No.: US 7,144,858 B2
(45) Date of Patent: Dec. 5, 2006

(54) ANTIBACTERIAL COMPOUNDS AND METHODS FOR TREATING GRAM POSITIVE BACTERIAL INFECTIONS

(75) Inventor: Dewey G. McCafferty, Plymouth Meeting, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/516,012

(22) PCT Filed: Jun. 2, 2003

(86) PCT No.: PCT/US03/17215

§ 371 (c)(1),
(2), (4) Date: Nov. 29, 2004

(87) PCT Pub. No.: WO03/101393

PCT Pub. Date: Dec. 11, 2003

(65) Prior Publication Data

US 2005/0233971 A1    Oct. 20, 2005

Related U.S. Application Data

(60) Provisional application No. 60/385,038, filed on May 31, 2002.

(51) Int. Cl.
*A61K 38/12* (2006.01)
*C12P 21/04* (2006.01)

(52) U.S. Cl. .................................. 514/9; 435/71.3
(58) Field of Classification Search ............ None
See application file for complete search history.

(56) References Cited

U.S. PATENT DOCUMENTS

| 4,427,656 A | 1/1984 | Cavalleri et al. |
| 5,539,087 A | 7/1996 | Restelli et al. |
| 5,752,941 A | 5/1998 | Romano et al. |
| 5,925,550 A | 7/1999 | Lancini et al. |

OTHER PUBLICATIONS

Loll, et al., J. med, Chem., 1999, 42, 4714-4719.*
Boger, D. L., "Vancomycin, Teicoplanin, and Ramoplanin: Synthetic and Mechanic Studies," Med. Res. Rev., 2001 Sep; 21(5): 356-81.
Jiang, W.; Wanner, J.; Lee, R. J.; Bounaud P. -Y.; and Boger, D. L., "Total Synthesis of the Ramoplanin A2 and Ramoplanose Aglycon," J.Am. Chem. Soc., May 15, 2002; 124(19).

* cited by examiner

*Primary Examiner*—Anish Gupta
*Assistant Examiner*—Satyanarayana R. Gudibande
(74) *Attorney, Agent, or Firm*—Nath & Associates PLLC; Gary M. Nath; Lee C. Heiman

(57) ABSTRACT

The present inventive subject matter relates to novel antibacterial compounds that are capable of inhibiting bacterial multiplication and killing living bacteria. The present inventive subject matter further relates to methods for treating Gram positive bacterial infections using the inventive compounds.

35 Claims, 6 Drawing Sheets

|   | $R_1$ | $R_2$ |
|---|---|---|
| 1 | α-D-Mannosyl-(1→2)-α-D-mannose | $NH_3^+$ |
| 2 | H | $NH_3^+$ |
| 3 | α-D-Mannosyl-(1→2)-α-D-mannose | $HNC(NH)NH_3^+$ |
| 4 | α-D-Mannosyl-(1→2)-α-D-mannose | $HN^+(CH_2)_2CH(CH_3)_2$ |
| 5 | α-D-Mannosyl-(1→2)-α-D-mannose | NHAc |
| 6 | α-D-Mannosyl-(1→2)-α-D-mannose | $NH_3^+$ (Lactone hydrolyzed) |

| | $R_1$ | $R_2$ |
|---|---|---|
| 1 | α-D-Mannosyl-(1→2)-α-D-mannose | $NH_3^+$ |
| 2 | H | $NH_3^+$ |
| 3 | α-D-Mannosyl-(1→2)-α-D-mannose | $HNC(NH)NH_3^+$ |
| 4 | α-D-Mannosyl-(1→2)-α-D-mannose | $HN^+(CH_2)_2CH(CH_3)_2$ |
| 5 | α-D-Mannosyl-(1→2)-α-D-mannose | NHAc |
| 6 | α-D-Mannosyl-(1→2)-α-D-mannose | $NH_3^+$ (Lactone hydrolyzed) |

H-L-Ala-D-γ-Glu-L-Lys-D-Ala-D-Ala-OH

| | $R_1$ | $R_2$ |
|---|---|---|
| 10 | L-Ala-D-γ-Glu-L-Lys-D-Ala-D-Ala-OH | UDP |
| 11 | L-Ala-D-γ-Glu-L-Dap-D-Ala-D-Ala-OH | UDP |
| 12 | L-Ala-D-γ-Glu-L-Dap-OH | UDP |
| 13 | L-Ala-D-γ-Glu-L-Dap-OH | $OPO_3^{2-}$ |
| 14 | OH | |
| 15 | L-Ala-D-γ-Gln | OH |

ANTIBACTERIAL COMPOUNDS AND METHODS FOR TREATING GRAM POSITIVE BACTERIAL INFECTIONS

This application claims the benefit of U. S. Provisional Patent Application No. 60/385,038, filed May 31, 2002, the contents of which is hereby incorporated by reference in its entirety.

This work was supported by National Institutes of Health grants, as well as by a National Institutes of Health National Research Service Award Fellowship. The United States government may have rights in this invention by virtue of this support.

BACKGROUND OF THE INVENTION

1. Field of the Invention

The present inventive subject matter relates to novel antibacterial compounds that are capable of inhibiting bacterial multiplication. The present inventive subject matter further relates to methods for treating Gram positive bacterial infections using the inventive compounds.

2. Background

Antibiotics and Antibiotic Resistance. Since their discovery in the 1930's, antibiotics have played a crucial role in the treatment of bacterial infections and diseases. However, with widespread use of broad-spectrum antibiotics, enormous selective pressures are placed on bacterial populations, provoking the evolution of resistance mechanisms and thus resistant bacterial strains. As a result, antibiotics are rendered less useful. In effect, antibiotic resistance results in increased health care costs, and morbidity and mortality from treatment failures.

The glycopeptide antibiotic vancomycin has been a drug of choice against Gram positive bacterial infections for almost thirty years. However, the use of vancomycin is now limited due to the development of resistance, especially notable in multidrug-resistant enterococcal and staphylococcal nosocomial pathogens.

Resistance of Gram positive bacteria to antibiotics is of great concern because of the human infections and diseases they can cause. For instance, Staphylococcus aureus can cause skin lesions, as well as severe infections such as pneumonia, meningitis, and urinary tract infections. Therefore, in the face of diminishing effectiveness of current antibiotics against resistant strains of Gram positive bacteria, a replacement for vancomycin is urgently needed. More generally, there is a continuing need for new and effective antibiotics.

U.S. Pat. No. 4,427,656, issued Jan. 24, 1984 to Cavalleri et al., discloses a chlorine-containing antibiotic substance called antibiotic A/16686 factor A2 in an essentially pure form. The process for the production of antibiotic A/16686 factor A2 by cultivation of an Actinoplanes bacterial strain and the co-produced antibiotic A/16686 factors A1 and A3 are also disclosed. Antibiotic A/16686 factors A1, A2, and A3, as well as the corresponding non-toxic physiologically acceptable acid addition salts are disclosed as antimicrobial agents which are active against gram-positive bacteria.

An improved method for isolating A/16686 is described in U.S. Pat. No. 5,925,550, issued Jul. 20, 1999 to Lancini et al., which discloses a method for selectively enhancing the production of factors A2 and/or A3 of antibiotic A/16686 either to isolate these single components or to enrich the complex in one or both the above components, and which comprises adding an appropriate precursor of the desired antibiotic factor to an A/16686 producing culture during fermentation.

U.S. Pat. No. 5,539,087, issued Jul. 23, 1996 to Restelli et al., discloses a process for recovering the antibiotics produced by the fermentation of an Actinoplanes species or an antibiotic producing mutant thereof, by extraction from a fermentation broth or a process stream.

A use for antibiotics of the ramoplanin group is described in U.S. Pat. No. 5,752,941, issued May 19, 1998 to Romano et al., which discloses central venous polyurethane catheters with a thin hydrophilic coating loaded with an antibiotic of the ramoplanin group, and their use in preventing catheter related infections. These catheters are useful to prevent bacterial adherence and colonization and, therefore, to lower the risk of vascular infections in catheterized patients. The method for preparing the catheter of the invention consists of incubating polyurethane catheters coated with a hydrophilic film in an aqueous solution of the selected antibiotic.

In Boger, D. L., Med. Res. Rev., 21:356–381 (2001) and Jiang, W.; Wanner, J.; Lee, R. J.; Bounaud, P.-Y.; and Boger, D. L., J. Am. Chem. Soc., 124:5288–5290 (2002), a solution-phase total synthesis of the aglycon of ramoplanin A2 and ramoplanose was reported. Three key protected peptide subunits were constructed and sequentially coupled to form a 17-residue linear protected peptide. This intermediate was subsequently cyclized between Phe9 and Orn10 to form the 49-membered macrocycle. This macrocyclization site was chosen to take advantage of the beneficial effects of β-sheet preorganization, as well as previous reports of efficient peptide macrolactamization at a D-amino acid terminus.

At present, there remains a need for new antibiotic substances, especially those which have greater antibacterial activity than current antibiotic compounds and/or reduced adverse side effects. The compounds of the present invention address this need in the art by providing antibiotic activity against both resistant and non-resistant strains of Gram positive bacteria, including vancomycin-resistant Enterococcus faecium and Enterococcus faecalis, and methicillin-resistant Staphylococcus aureus, as well as other bacteria resistant to ampicillin and erythromycin.

This and other features of the invention will be apparent from the detailed description of the inventive subject matter and the claims.

SUMMARY OF THE INVENTION

The present inventive subject matter relates to a compound of Formula I:

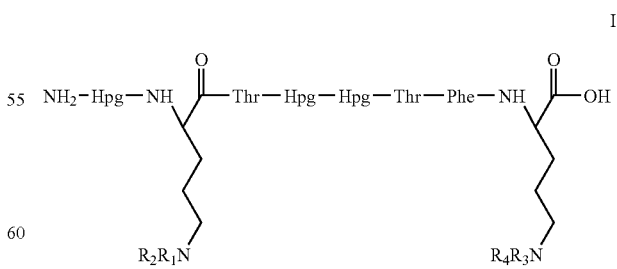

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-$Me_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

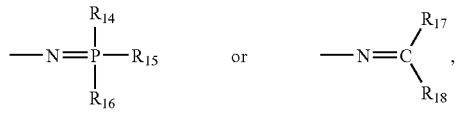

or are taken together with the nitrogen associated with each pair of $R_1$ and $R_2$ and/or $R_3$ and $R_4$, to form a ring in

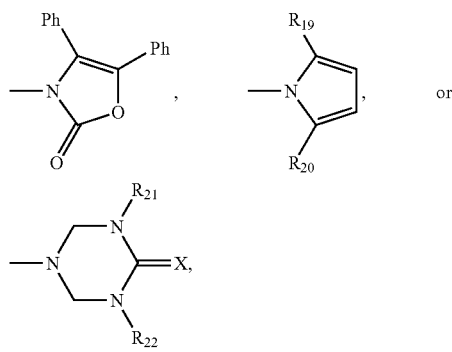

or $R_1$ and $R_2$, $R_3$ and $R_4$, or both $R_1$ and $R_2$, and $R_3$ and $R_4$, are independently replaced by a stable quaternary ammonium salt complex of Formula III:

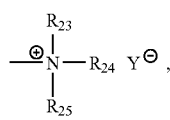

III and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

n is 1–9;

X is O or S;

Y is F, Cl, Br, or I;

Ar is a mono-, bi- or tricyclic, carbo- or heterocyclic ring; wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl.

The present inventive subject matter further relates to a compound of Formula II:

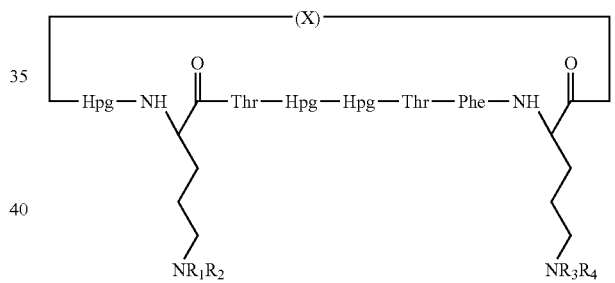

II wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen -atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-$Me_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

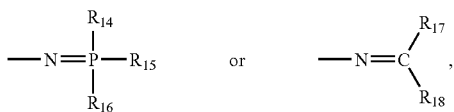

or are taken together with the nitrogen associated with each pair of $R_1$ and $R_2$ and/or $R_3$ and $R_4$, to form a ring in

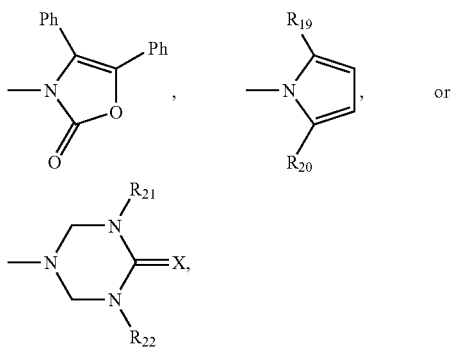

or $R_1$ and $R_2$, $R_3$ and $R_4$, or both $R_1$ and $_2$ and $R_3$ and $R_4$, are independently replaced by a stable quaternary ammonium salt complex of Formula III:

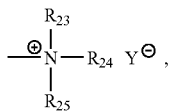

III and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:
straight or branched $C_1$–$C_9$ alkyl,
straight or branched chain $C_1$–$C_9$, alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar,
straight or branched chain $C_2$–$C_9$ alkenyl or alkynyl, and
straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;
n is 1–9;
X is O or S;
Y is F, Cl, Br, or I;
Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and
$R_5$ and $R_6$ are independently selected from the group consisting of hydrogen and straight or branched chain $C_1$–$C_6$ alkyl,
provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;
$R_5$ and $R_6$ are independently selected from the group consisting of hydrogen and straight or branched chain $C_1$–$C_6$ alkyl; and
X is a spacer that is less than about 100 Angstroms.

The present inventive subject matter further relates to a method for treating a Gram positive bacterial infection in an animal, which comprises administering to said animal an effective amount of a compound of Formula I:

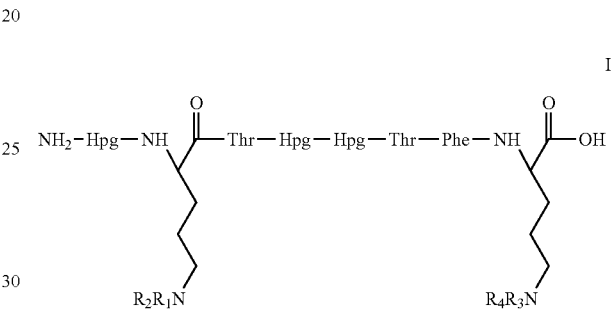

I wherein:
$R_1$, $R_2$, $R_3$ and $R_4$ are independently selected from the group consisting of:
hydrogen,
straight or branched chain $C_1$–$C_9$ alkyl,
straight or branched chain $C_1$–$C_9$ alkyl, wherein 1 to 3 hydrogen atoms attached to a carbon atom of said alkyl is/are replaced with $NR_5R_6$,
—C(O)—O—$R_8$,
—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)$ $C(X)$—,
—S(O)(O)—$R_{10}$.
—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$,
—P(X)—$R_{12}$, wherein $R_{12}$ is selected from the group consisting of Ph, $CH_3$, PhO, BnO, and iPrO,
—C(X)—NH—$R_{13}$, and
—$(CH_2)_m$—Si-Me$_3$, or
$R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

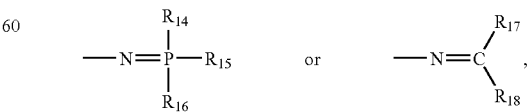

or are taken together with the nitrogen associated with each pair of $R_1$ and $R_2$ and/or $R_3$ and $R_4$, to form a ring in

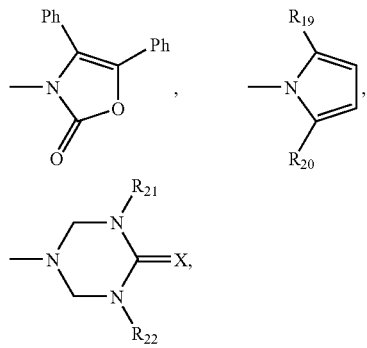

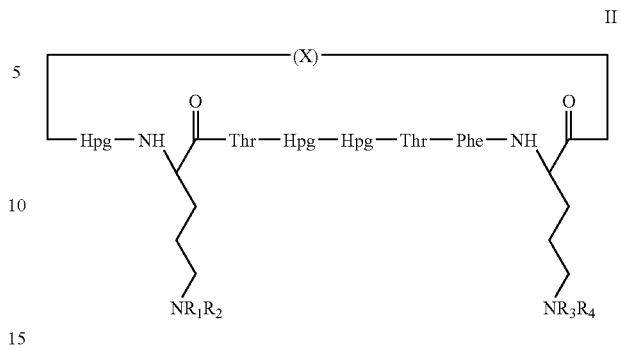

or $R_1$ and $R_2$, $R_3$ and $R_4$, or both $R_1$ and $R_2$, and $R_3$ and $R_4$, are independently replaced by a stable quaternary ammonium salt complex of Formula III:

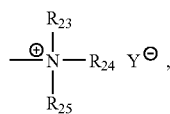

and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

n is 1–9;

X is O or S;

Y is F, Cl, Br, or I.

Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl.

The present inventive subject matter additionally relates to a method for treating a Gram positive bacterial infection in an animal, which comprises administering to said animal an effective amount of a compound of Formula II:

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-Me$_3$, or $R_1$ and: $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

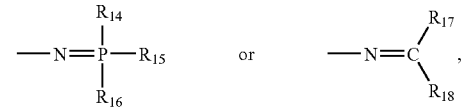

or are taken together with the nitrogen associated with each pair of $R_1$ and $R_2$ and/or $R_3$ and $R_4$, to form a ring in

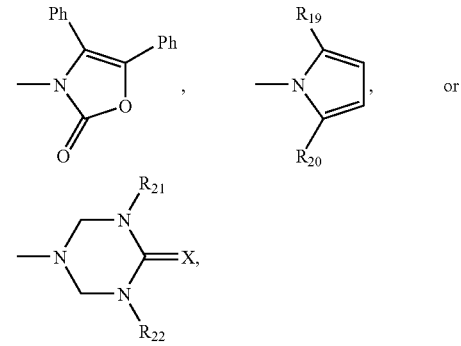

or $R_1$ and $R_2$, $R_3$ and $R_4$, or both $R_1$ and $R_2$, and $R_3$ and $R_4$, are independently replaced by a stable quaternary ammonium salt complex of Formula III:

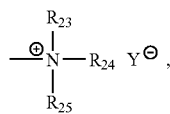

and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:
straight or branched $C_1$–$C_9$ alkyl,
straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar,
straight or branched chain $C_2$–$C_9$ alkenyl or alkynyl, and
straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;
n is 1–9;
X is O or S;
Y is F, Cl, Br, or I;
Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and
$R_5$ and $R_6$ are independently selected from the group consisting of hydrogen and straight or branched chain $C_1$–$C_6$ alkyl,
provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;
$R_5$ and $R_6$ are independently selected from the group consisting of hydrogen and straight or branched chain $C_1$–$C_6$ alkyl; and
X is a spacer that is less than about 100 Angstroms.

DETAILED DESCRIPTION OF THE INVENTION

Definitions

Figure 1:
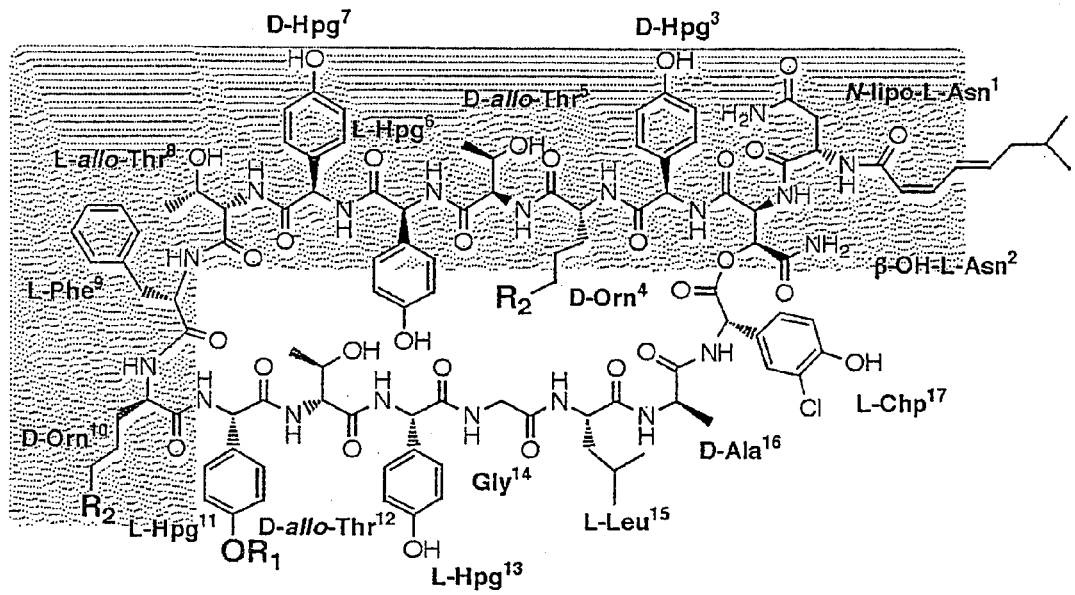
FIG. 1 is a drawing which depicts the chemical structure of the cyclic form of compounds of the present invention having the $R_1$ and $R_2$ substitutions shown.

The term "animal" refers to a multicellular organism of the kingdom Animalia, differing from plants in certain typical characteristics such as capacity for locomotion, non-photosynthetic metabolism, pronounced response to stimuli, restricted growth, and fixed bodily structure. The term "animal" more particularly relates to mammals, and most particularly relates to humans.

The term "amino acid" refers to any organic acid containing one or more amino substituents. The term is usually restricted to amino, especially α-amino, derivatives of aliphatic carboxylic acids, but it can also include β-amino derivatives.

The term "spacer" as used herein refers to a stretch of atoms of specified length which separates and/or surrounds one or more moieties having particular characteristic(s) of interest. In this application, a preferred spacer may be a series of atoms, for example a substituted or unsubstituted, saturated or unsaturated, hydrocarbon chain, optionally substituting heteroatoms such as N, O, or S for carbon atoms in the chain, or particularly a series of natural or synthetic amino acids.

The term "MurNAc" refers to the compound N-acetylmuramyl.

The term "peptidoglycan" refers to the thick rigid layer that is a component of the bacterial cell wall, the presence of which is critical for survival of the bacteria. The peptidoglycan layer is composed of an overlapping lattice of 2 sugars that are crosslinked by amino acid bridges.

The term "lipid I" refers to undecaprenyl-pyrophosphoryl-acetylmuramyl-pentapeptide, a monomer which is an intermediate utilized in the biosynthesis of peptidoglycan of bacterial cell walls.

The term "lipid II" refers to undecaprenyl-pyrophosphoryl-N-acetylmuramyl(-acetylglucoseamine)-pentapeptide, a monomer which is an intermediate utilized in the biosynthesis of peptidoglycan of bacterial cell walls.

The term "bacterial multiplication" refers to bacterial growth, colonization, division, infection, disease, subsistence, adherence, or any one or combinations of these or other terms used to imply the survival of bacteria.

The term "nosocomial pathogen" refers to a bacterial pathogen which causes a nosocomial infection, which is an infection not present at the time of patient admission, but originating from exposure to a hospital environment.

The term "A/16686" refers to peptide antibiotic ramoplanin.

The term "sequester" or "sequestration" refers to the process of setting apart, isolating, or keeping away from.

The terms "Orn" and "ornithine" refer to a synthetic amino acid having the structure:

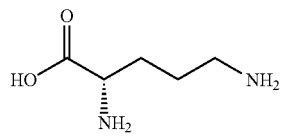

The terms "Hpg" and "hydroxyphenylglycine" refer to a synthetic amino acid having the structure:

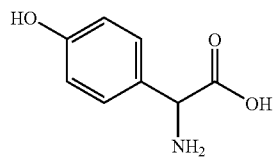

The term "Ala" refers to the amino acid alanine.
The term "Glu" refers to the amino acid glutamate.
The term "Thr" refers to the amino acid threonine. Threonine has two chiral centers: the α-carbon and the β-carbon, so there are four different enantiomers: L-Threonine, which is the enantiomer (2S,3R)-(−)-threonine, L-allo-Threonine, which is the enantiomer (2S,3S)-(+)-allo-threonine, D-allo-Threonine, which is the enantiomer (2R,3R)-(−)-allo-threonine, and D-Threonine, which is the enantiomer (2R,3S)-(+)-threonine.

The term "Phe" refers to the amino acid phenylalanine.

The term "Asn" refers to the amino acid asparagine.
The term "Chp" refers to a synthetic amino acid 3-chloro-4-hydroxyphenylglycine.

Compounds of the Present Invention

Addressing the need in the art for new antibiotic compounds, the compounds of the present invention are effective against both resistant and non-resistant strains of Gram positive bacteria, including vancomycin-resistant *Enterococcus faecium* and *Enterococcus faecalis*, and methicillin-resistant *Staphylococcus aureus*, as well as other bacteria resistant to ampicillin and erythromycin. A feature of the compounds of the present invention that renders them effective against resistant strains of Gram positive bacteria is their ability to recognize and bind a structural motif of peptidoglycan intermediates which is different than that targeted by antibiotics like vancomycin.

Thus, the present inventive subject matter relates to compounds that bind to lipid I, lipid II, and other intermediates involved in peptidoglycan (hereinafter "PG") biosynthesis. The inventive compounds are highly effective against Gram positive bacteria, especially those which are antibiotic-resistant. In particular, the compounds of the present invention contain an octapeptide domain which recognizes the structural motif MurNAc-Ala-γ-Glu pyrophosphate, rather than the conventional N-acyl-DAla-DAla motif recognized by vancomycin and other similar glycopeptide antibiotics, which recognize and bind to PG biosynthesis intermediates. This recognition and binding ability overcomes the adaptions which drug resistant bacteria have evolved. Further, without being bound to a particular mechanism of action, we believe that upon complexation with these intermediates, the inventive compounds are involved in a ligand-induced aggregation to produce insoluble fibrils. It is expected that such fibrils are flat or twisted ribbon structures of about 5 nm in width and 100 nm in length.

At each step, PG biosynthesis and assembly are controlled by enzymes. Synthesis of PG can be divided into two steps. The first step involves the formation of N-acetyl glucosamine-N-muramic acid (NAG-NAM) peptide monomers that make up PG. The second step involves the polymerization of the NAG-NAM-peptide monomers to a nascent PG chain and then addition to the existing cell wall PG.

It is expected that the inventive compounds do not target the PG biosynthesis enzymes directly, but rather that a mechanism for sequestration of PG intermediates prevents these monomers from being properly used as substrates by late-stage PG biosynthesis enzymes MurG and the transglycosylases. As a result, treated bacteria produce a mechanically weakened cell wall. Since the presence of a thick and rigid layer of PG is critical for the survival of bacteria, it is expected that the sequestration event ultimately causes bacterial cell death. However, this does not exclude the possibility that the mechanism of action may be otherwise, such as the destruction of the structural integrity of PG intermediates after binding to the inventive compounds such that the incorporation of these monomers into the PG chain and/or layer results in a weak or dysfunctional bacterial cell wall. Further, it is expected that the insoluble fibrils hinder the PG biosynthesis machinery by aiding the capture of PG intermediates.

Thus, the inventive subject matter relates to a compound of Formula I:

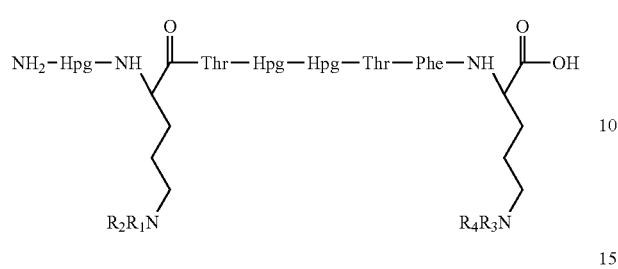

wherein:

R$_1$, R$_2$, R$_3$ and R$_4$ are independently selected from the group consisting of:
hydrogen,
straight or branched chain C$_1$–C$_9$ alkyl,
straight or branched chain C$_1$–C$_9$ alkyl, wherein 1 to 3 hydrogen atoms attached to a carbon atom of said alkyl is/are replaced with NR$_5$R$_6$,
—C(O)—O—R$_8$,
—C(O)—R$_9$, wherein R$_9$ is selected from the group consisting of CH$_3$C(X)—, CF$_3$C(X)—, CBr$_3$C(X)—, CCl$_3$C(X)—, and CH$_3$(CH$_2$)$_n$C(X)—,
—S(O)(O)—R$_{10}$,
—S—R$_{11}$, wherein R$_{11}$ is selected from the group consisting of C$_6$H$_5$, C$_6$Cl$_5$, C$_6$H$_4$-o-NO$_2$, —S—C$_6$H$_3$-2,4-(NO$_2$)$_2$, AND C(C$_6$H$_5$)$_3$,
—P(X)—R$_{12}$, wherein R$_{12}$ is selected from the group consisting of Ph, CH$_3$, PhO, BnO, and iPrO,
—C(X)—NH—R$_{13}$, and
—(CH$_2$)$_m$—Si-Me$_3$, or R$_1$ and R$_2$ are taken together, R$_3$ and R$_4$ are taken together, or both R$_1$ and R$_2$, and R$_3$ and R$_4$, are taken together with the nitrogen associated with each pair of R$_1$ and R$_2$ and/or R$_3$ and R$_4$, to form a double bond in

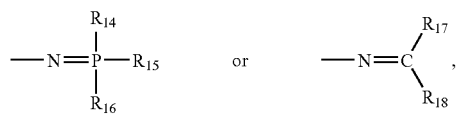

or are taken together with the nitrogen associated with each pair of R$_1$ and R$_2$ and/or R$_3$ and R$_4$, to form a ring in

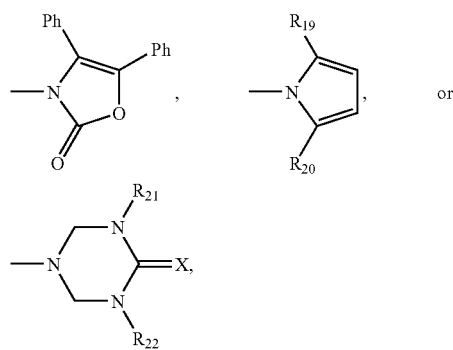

or R$_1$ and R$_2$, R$_3$ and R$_4$, or both R$_1$ and R$_2$, and R$_3$ and R$_4$, are independently replaced by a stable quaternary ammonium salt complex of Formula III:

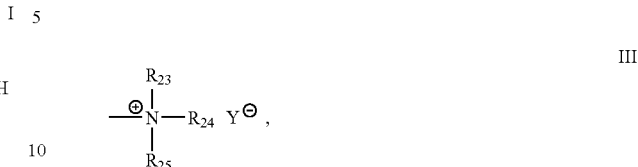

and wherein R$_8$, R$_{10}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, and R$_{25}$, are independently selected from the group consisting of:
straight or branched C$_1$–C$_9$ alkyl,
straight or branched chain C$_1$–C$_9$ alkyl substituted with one or more halo, trifluoromethyl, nitro, C$_1$–C$_6$ straight or branched chain alkyl, C$_2$–C$_6$ straight or branched chain alkenyl, hydroxy, C$_1$–C$_4$ alkoxy, C$_2$–C$_4$ alkenyloxy, phenoxy, benzyloxy, amino, or Ar,
straight or branched chain C$_2$–C$_9$ alkenyl or alkynyl, and
straight or branched chain C$_2$–C$_9$ alkenyl or alkynyl substituted with one or more halo, trifluoromethyl, nitro, C$_1$–C$_6$ straight or branched chain alkyl, C$_2$–C$_6$ straight or branched chain alkenyl, hydroxy, C$_1$–C$_4$ alkoxy, C$_2$–C$_4$ alkenyloxy, phenoxy, benzyloxy, amino, or Ar;

n is 1–9;

X is O or S;

Y is F, Cl, Br, or I;

Ar is a mono-, bi- or tricyclic, carbo- or heterocyclic ring, wherein the ring is either unsubstituted or substituted in one or more position(s) with halo, hydroxyl, nitro, trifluoromethyl, C$_1$–C$_6$ straight or branched chain alkyl or alkenyl, C$_1$–C$_4$ alkoxy, C$_1$–C$_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and R$_5$ and R$_6$ are independently selected from the group consisting of hydrogen and straight or branched chain C$_1$–C$_6$ alkyl.

In another aspect of the inventive subject matter, said Ar is selected from the group consisting of fluorenyl, naphthyl, indolyl, thioindolyl, furyl, thiazolyl, thienyl, pyridyl, quinolinyl, isoquinolinyl, phenyl, and benzyl.

In the inventive compounds, ornithine, as a primary amine, is optionally modified using a variety of specific protecting groups to produce the compound derivatives of the inventive subject matter described above.

In a preferred embodiment, R$_8$ is selected from the group consisting of fluorenyl, tert-butyl, benzyl, phenyl, and trichloroethyl. Thus, as depicted in Scheme I, a variety of alky and aryl carbamates are formed by reaction in basic pH of the amino group of ornithine and either a succinimidyl carbonate or a chlorocarbonate.

SCHEME I

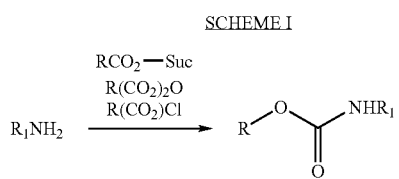

wherein $CO_2R$ is Fmoc, t-Boc, Cbz, Alloc, Phenoc, Troc, or other oxycarbonyl compound.

As depicted in Scheme II, amides are obtained by reaction of amino group of ornithine with mostly symmetric anhydrides or acylhalides. Basic pH is desirable to perform the acylation. It should be noted that care has to be taken to avoid O-acylation, should hydroxyl groups be present in the reactive compounds. Reaction with oxalychloride or analogue derivatives lead to cyclic bisamides.

SCHEME II

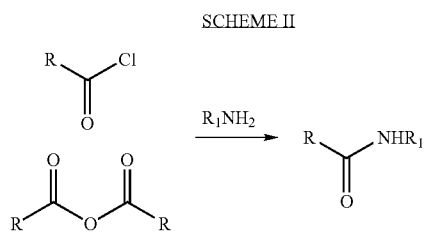

wherein, for example, R is $CH_3C(O)$, $CF_3C(O)$, $CBr_3C(O)$, $CCl_3C(O)$, $—(CO)(CH_2)nC(O)—$, or $CH_3C(S)$.

As depicted in Scheme III, sulfonamides are obtained by reacting substituted aryl or alkyl sulfonyl chloride with ornithine amino group in presence of pyridine or aqueous base. The resulting methylsulfonamide is optionally transformed to an amino sulfonic acid by further reaction with lithium hydroxide.

SCHEME III

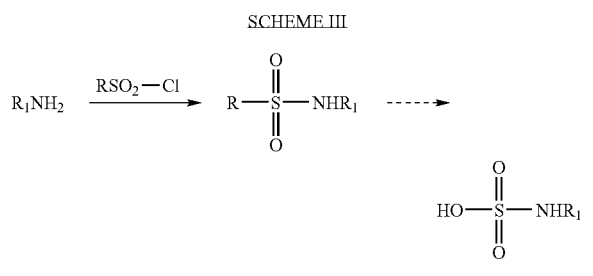

wherein, for example, R is Ar, Me, $CF_3$, or $[(CF_3SO_2)_2)]$.

As depicted in Scheme IV, sulfenamides, mostly arylsulfenyl halides, are used for the protection of amines into sulfenamides. Sulfenamides are less stable than sulfonamides.

SCHEME IV

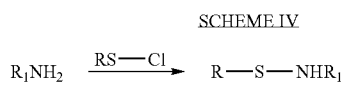

wherein, for example, R is $C_6H_5$, $C_6Cl_5$, $C_6H_4$-o-$NO_2$, $—S—C_6H_3$-2,4-$(NO_2)_2$, or $C(C_6H_5)_3$.

As depicted in Scheme V, phosphonamidates, phosphinamides, and thiphosphimamides are obtained from chlorophosphates or chlorophosphine oxides or sulfides in presence of triethylamine.

SCHEME V

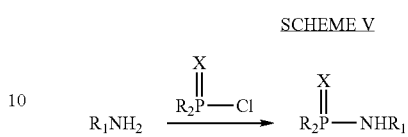

wherein, for example, for Phosphonamidates: X is O; R is PhO, BnO, or iPrO; for Phosphineamides: X is O; R is Ph; and for Thiophosphineamides: X is S; R is Ph or $CH_3$.

As depicted in Scheme VI, phosphazenes or iminophosphoranes are formed by reaction, for example, of primary amines and dibromotriphenylphosphorane in the presence of organic bases.

SCHEME VI

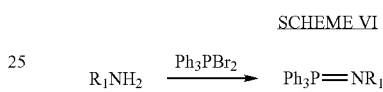

As depicted in Scheme VII, oxazolinones are formed by reaction, for example, of a primary amine and a dioxolinone.

SCHEME VII

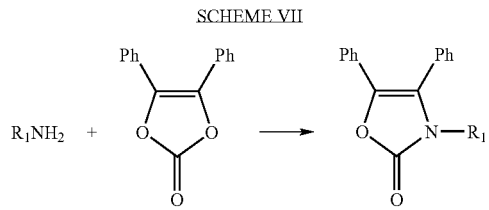

As depicted in Scheme VIII, pyrrole derivatives are formed by reaction of a primary amine with, for example, 2,5-Hexanedione in acetic acid.

SCHEME VIII

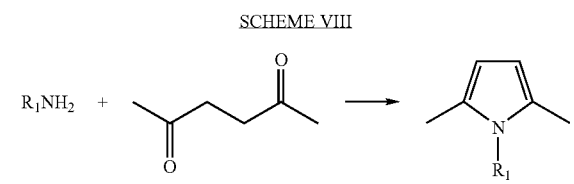

As depicted in Scheme IX, imines are formed by reaction of a primary amine with ketones.

SCHEME IX

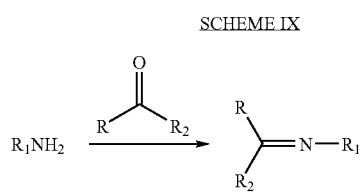

As depicted in Scheme X, ureas and thioureas are obtained by reacting a primary amine with isocyanates or thioisocyanates.

SCHEME X

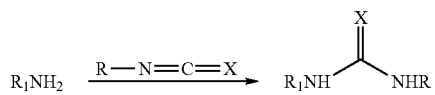

wherein, for example, R=Ar, X=O or S.

As depicted in Scheme XI, triazacyclohexanones are produced by reacting ureas or thioureas with primary amines.

SCHEME XI

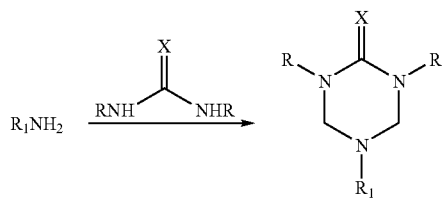

wherein, for example, R=CH$_3$ or C$_6$H$_5$; X=O or S.

As depicted in Scheme XII, reductive alkylation is required to obtain alkylamines, such as monoalkyl ornithine. Aldimines are subject to Sodium Cyano Borhydride in presence of Ni Raney catalyst.

SCHEME XII

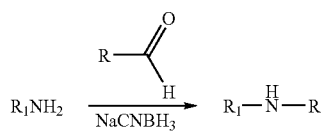

wherein, for example, R=H, CH$_3$, C$_2$H$_6$, C$_3$H$_7$, other alkyl, or Aryl.

As depicted in Scheme XIII, quaternary ammonium salts are produced by reacting an excess of, for example, methyl iodide with ornithines, for example producing a stable quaternary iodide salt.

SCHEME XIII

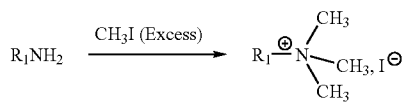

As depicted in Scheme XIV, silyl reagents are used for amine-protection to produce exemplary metalloamines. The reactions must be performed under strictly anhydrous conditions due to the sensitivity of N—Si bonds to moisture.

SCHEME XIV

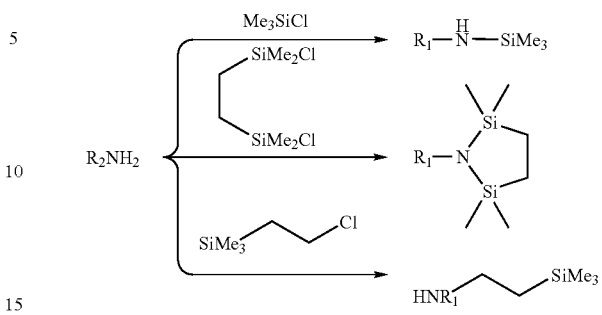

As depicted in Scheme XV, guanidino-ornithines are produced by reacting primary amines with, for example, 1-pyrazole-carboxamidine in the presence of HCl.

SCHEME XV

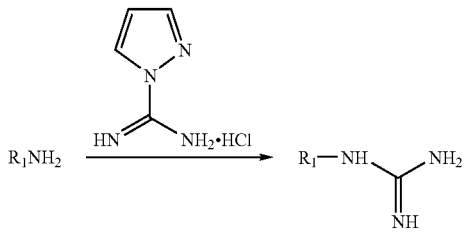

In another preferred embodiment, R$_1$, R$_2$, R$_3$, and R$_4$ are independently selected from the group consisting of:
hydrogen,
straight or branched chain C$_1$–C$_6$ alkyl, and
straight or branched chain C$_1$–C$_6$ alkyl wherein 1 to 3 hydrogen atoms attached to a carbon atom of said alkyl is/are replaced with NR$_5$R$_6$; and
R$_5$ and R$_6$ are independently selected from the group consisting of hydrogen and straight or branched chain C$_1$–C$_6$ alkyl.

In another aspect of the inventive subject matter, the compound is: H$_2$N-Hpg-Orn-Thr-Hpg-Hpg-Thr-Phe-Orn-COOH.

In another aspect of the inventive subject matter, the compound binds to a structural motif of the Formula: MurNAc-Ala-γ-Glu pyrophosphate.

In a more preferred embodiment, the compound which binds to the structural motif has a K$_d$ greater than or equal to about 90 μM.

In another more preferred embodiment, the K$_d$ ranges from about 100 μM to about 3.0 mM.

Without being bound to a particular mechanism of action, we believe that the compounds of the present invention interfere with synthesis of the monomers of PG. That process begins by activating NAG with the addition of uracil diphosphate, which serves as a carrier of the growing PG during its synthesis. Along the way various intermediates are formed and then converted to subsequent intermediates which ultimately lead to the formation of lipid I (undecaprenyl-pyrophosphoryl-N-acetylmuramyl-pentapeptide).

Then, lipid I is converted by MurG enzymes to the lipid II monomer (undecaprenyl-pyrophosphoryl-N-acetylmuramyl (N-acetylglucosamine)-pentapeptide). Subsequently, lipid II monomers are added to the growing peptidoglycan. Each monomer is attached to the bacterial cell PG by a transglycosylation reaction using Tgases. Finally, the growing peptidoglycan chain is cross-linked by transpeptidases that form covalent links between the peptide side chains.

The inventive compounds are capable of recognizing and binding to at least one structural motif having the formula of MurNAc-Ala-γ-D-Glu pyrophosphate common among various intermediates of PG biosynthesis, including lipid I and II. We have found that the inventive compounds can recognize and complex with PG intermediates that possess such a motif and prevent these intermediates from being properly used as substrates by the PG biosynthesis enzymes. As a result, PG biosynthesis is hindered. Because the binding locus is different than that recognized by conventional glycopeptide antibiotics, such as vancomycin, the inventive compounds are effective even against resistant strains of Gram-positive bacteria.

Figure 4:
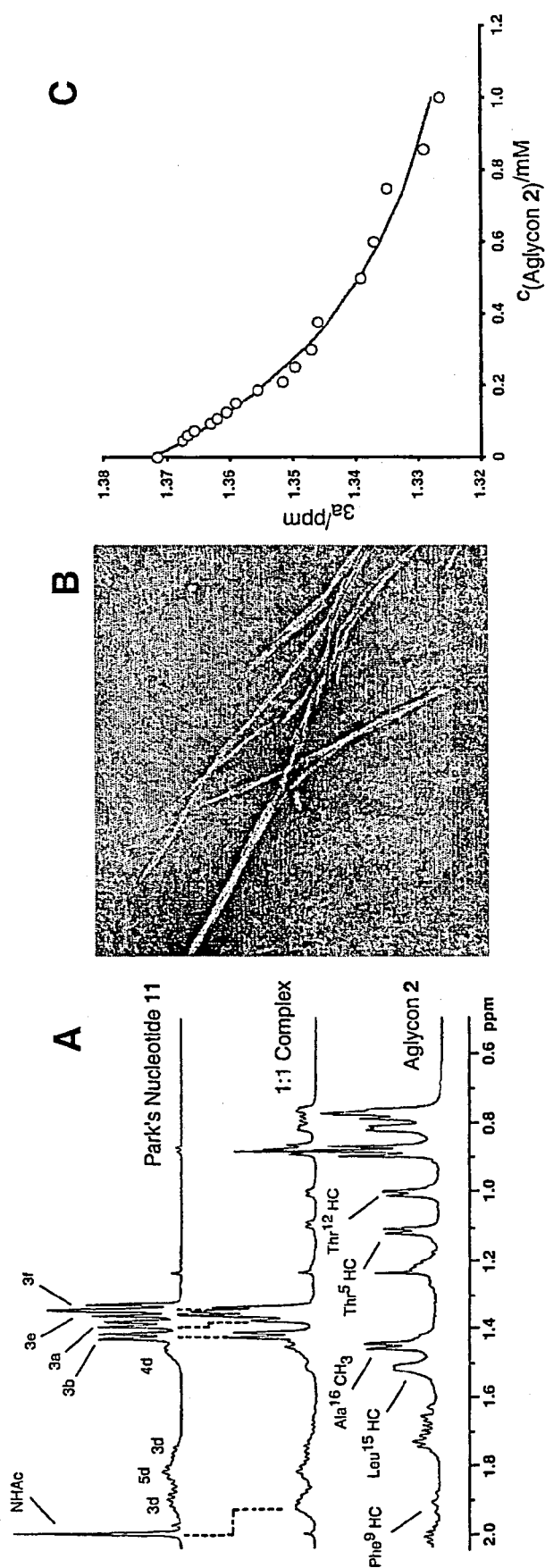
FIG. 4A is a graph which depicts part of the aliphatic region of the $^1$H NMR spectrum showing the chemical shift changes that occur upon binding of a compound of the present invention, free Park's nucleotide, and a 1:1 mixture of the two.
FIG. 4B is a representative transmission electron micrograph of the fibrils formed from the complexation of a compound of the present invention with Park's nucleotide.
FIG. 4C is a graph which depicts is a representative $K_d$ determination plot of the binding of a compound of the present invention to Park's nucleotide as obtained by $^1$H NMR titration.
Figure 6:
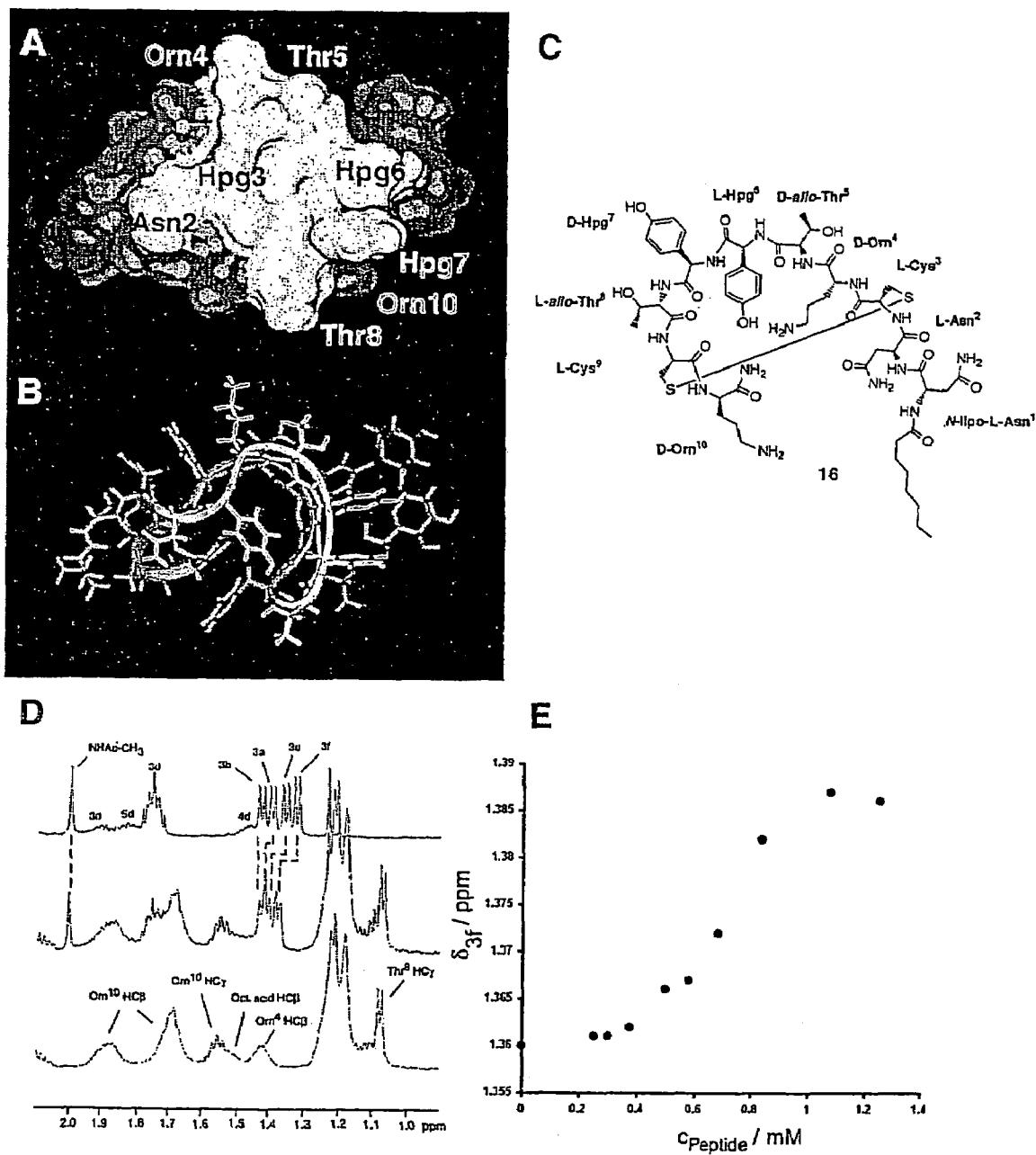
FIG. 6A is a drawing which depicts the surface representation of a compound of the present invention based on the NMR solution structure obtained in 20% DMSO.
FIG. 6B is a drawing which depicts a stick representation of the structure of the cyclic form of a compound of the present invention showing that the residues comprising the binding interface lie along one of the two beta strands emanating from the Thr$^6$-Phe$^7$ Type I beta turn.
FIG. 6C is a drawing which depicts the structure of a disulfide-linked conformationally-constrained peptide of the present invention showing the structural and functional elements of the peptidoglycan intermediate capture motif.
FIG. 6D is a graph which depicts a part of the aliphatic region of the $^1$H NMR spectrum of a second compound of the present invention (bottom trace), free Park's nucleotide (top trace), and a 1:1 mixture of the two (middle trace) depicting the chemical shift changes that occur upon binding.
FIG. 6E is a graph which depicts a plot of binding of a compound of the present invention to Park's nucleotide, as a function of the concentration of the inventive compound as obtained by $^1$H NMR titration.

Lipid I and II, as well as UDP-MurNAc-L-Ala-γ-D-Glu-L-Dap-D-Ala-D-Ala pentapeptide and UDP-MurNAc-L-Ala-γ-D-Glu-L-Dap tripeptide, both cytoplasmic PG biosynthetic precursors on the pathway for Lipid II biosynthesis, contain a structural motif recognized by the inventive compounds. Although it is expected that lipid II is the physiologically relevant intermediate targeted, we expect that these other intermediates complex with the inventive compounds and form insoluble fibrils. As shown in FIGS. 4 and 6B, the inventive compounds are capable of binding and undergoing ligand-induced fibril formation with UDP-MurNAc-L-Ala-γ-D-Glu-L-Dap-D-Ala-D-Ala pentapeptide (Park's nucleotide) and citronellyl-lipid I.

Figure 2:
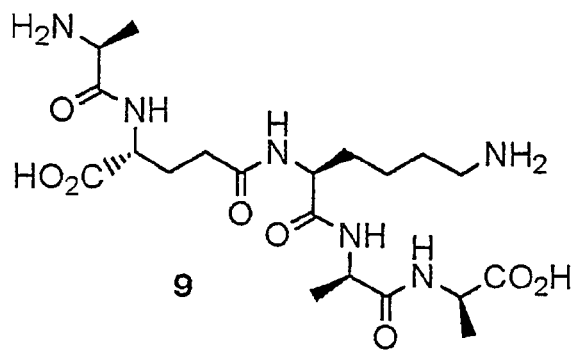
FIG. 2 is a drawing which depicts the chemical structures of synthetic analogues of bacterial peptidoglycan monomers used in the Examples herein.
Figure 2:
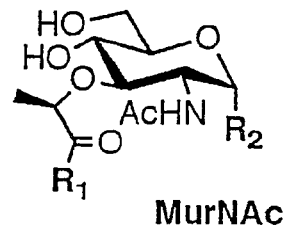

The components of a motif for recognition by the inventive compounds include a MurNAc sugar containing a 1'-pyrophosphate, an intact amide bond between the 3'-lactyl ether side chain of the carbohydrate and the pendant L-alanine moiety of the pentapeptide. Each substructure contributes to form a minimal recognition motif capable of recognition and binding by the present antibacterial compounds which then undergo ligand-induced fibril formation. All three analogues of PG intermediates shown in FIG. 2 are capable of recognition and binding to the inventive compounds, because each analogue contains the motif.

It is expected that the inventive compounds anchor to the bacterial cell membrane through their hydrophobic amino acid residues, where they bind to the PG intermediates in the membrane bilayer. It is expected that several side chain hydroxyls within each of the inventive compounds assist in the capture of the muramyl carbohydrate of PG precursors. Threonine residues in positions 3 and 6, along with hydroxyphenylglycine residues in positions 4 and 5, of the inventive compounds play a role in sequestration of the muramyl carbohydrate while the ornithine residues in positions 2 and 8 orient and stabilize the ligand in this complex.

The ornithine residues are positively charged due to the cationic charges on their γ-amino groups. Therefore, we expect that the ornithines interact with the anionic lipid I and II pyrophosphate and/or peptidyl carboxylates and other negatively charged portions of PG intermediate ligands. It is expected that the ornithine residues in positions 2 and 8 anchor the PG intermediate ligand in the proper orientation for binding using electrostatic or hydrogen bonding interactions. Ornithine residues of the inventive compounds which are modified at their γ-amino groups are also positively charged, and thus function similarly in anchoring and orienting the PG ligand. We expect that the preservation of charge on these ornithine residues enhance the antibacterial activity of the inventive compounds. Positions 2 and 8 of the inventive compounds can tolerate a number of diverse substitutions, providing they maintain a positive charge at these sites.

Without being bound to a particular mechanism of action, we believe that upon binding to the PG intermediates, the inventive compounds undergo a conformational change resulting in the exposure of a hydrophobic core containing hydroxyphenylglycine and phenylalanine, creating an exposed hydrophobic face capable of dimerization and oligomerization with other complexes. The ligand-induced exposure of the hydrophobic core is expected to lead to fibril formation.

Figure 3:
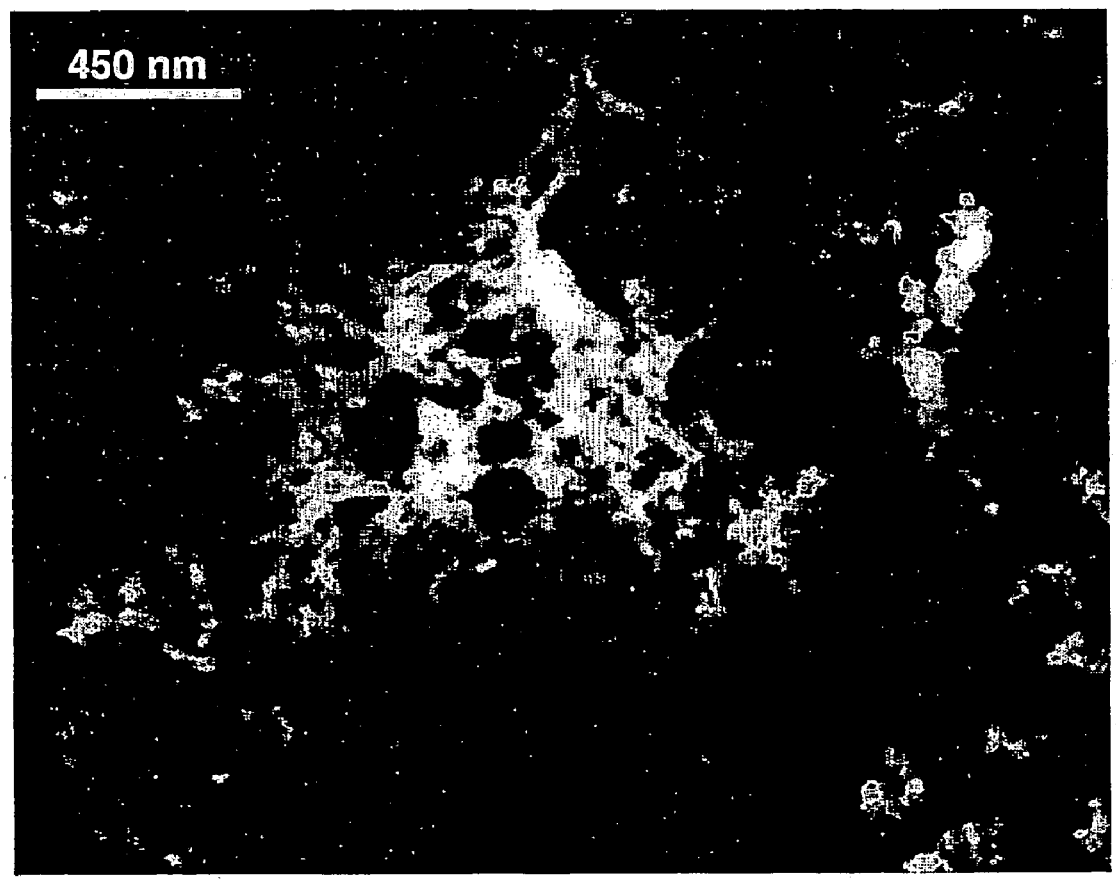
FIG. 3 is a transmission electron micrograph of the aggregate formed from the complexation of a compound of the present invention with 0.5 mM UDP-MurNAc-L-Ala-γ-D-Glu-L-Dap-D-Ala-D-Ala pentapeptide (Park's nucleotide).

Fibril formation is observed in vitro and serves as a convenient predictor of PG complexation in vitro. As shown in FIG. 3, upon mixing equimolar homogenous solutions of the inventive compounds with Park's nucleotide, which is a cytoplasmic PG biosynthetic precursor of lipid II, an amorphous precipitate formed immediately. It is found that the fibrils can be solubilized with 20% dimethyl sulfoxide (DMSO) while preserving modest binding affinity between the inventive compounds and PG intermediate ligands. Therefore, DMSO allows for the determination of binding affinity ($K_d$) values and characterization of the binding interface by Nuclear Magnetic Resonance spectroscopy (NMR).

Without being bound to a particular mechanism of action, we believe that fibril formation can also occur at the membrane level, and not just in vitro, but also in free solution. In a membrane environment, such as that of bacterial cells, the insoluble fibrils are expected to impart beneficial effects, including improved capture of both PG monomers and actively polymerizing PG chains.

The amino acid residues of the inventive compounds may be further modified in a number of ways, including chlorinations acylations with cis and/or trans saturated and/or unsaturated fatty, acids and glycosylations. Glycosylations can be done with monosaccharides, including mannose, and with disaccharides or polysaccrides.

These modifications are expected to stabilize the conformation of the inventive compounds. Stability of the inventive compounds is observed by decreased conformational flexibility and susceptibility to acid hydrolysis. The time-dependent decomposition in acidic solutions of the inventive compounds in non-modified form displayed rapid decomposition in neat trifluoroacetic acid ("TFA") and modest rates of decomposition in 0.1% aqueous TFA and when exposed to solutions containing 1 to 10% hydrochloric acid or acetic acid. However, when the inventive compounds were glycosylated they were resistant to acid hydrolysis over similar time regimes and conditions examined. In effect, these modifications ensure antibiotic integrity in low pH extracellular environments and protects the present antibacterial compounds from deleterious proteolytic degradation. It is expected that as a result, by stabilizing and protecting the inventive compounds, these modifications in turn help to improve the antibacterial activity of the compounds of the present invention.

The present inventive subject matter further relates to a compound of Formula II:

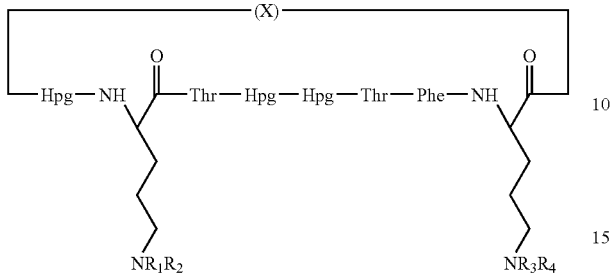

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-Me$_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

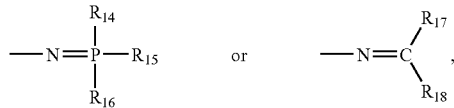

or are taken together with the nitrogen associated with each pair of $R_1$ and $R_2$ and/or $R_3$ and $R_4$, to form a ring in

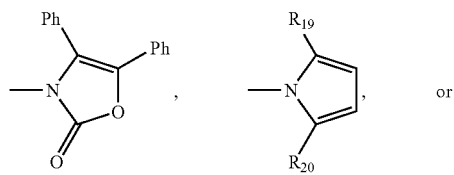

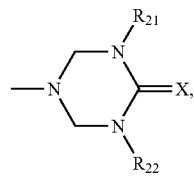

or $R_1$ and $R_2$, $R_3$ and $R_4$, or both $R_1$ and $R_2$, and $R_3$ and $R_4$, are independently replaced by a stable quaternary ammonium salt complex of Formula III:

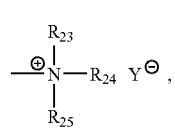

and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy,- amino, or Ar;

n is 1–9;

X is O or S;

Y is F, Cl, Br, or I;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl, provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;

$R_5$ and $R_6$ are independently selected from the group consisting of hydrogen and straight or branched chain $C_1$–$C_6$ alkyl; and X is a spacer that is less than about 100 Angstroms.

In a preferred embodiment, X is a spacer that is about 20 Angstroms. However, it will understood that X is optionally as small as a direct bond between the Hpg and Orn residues which it bridges.

In another aspect, $R_1$, $R_2$, $R_3$, and $R_4$ are independently selected from the group consisting of:
hydrogen,
straight or branched chain $C_1$–$C_6$ alkyl, and
straight or branched chain $C_1$–$C_6$ alkyl wherein 1 to 3 hydrogen atoms attached to a carbon atom of said alkyl is/are replaced with $NR_5R_6$,
provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;
$R_5$ and $R_6$ are independently selected from the group consisting of hydrogen and straight or branched chain $C_1$–$C_6$ alkyl; and
X is a spacer that is less than about 100 Angstroms.

In a preferred embodiment, X is within the range from about 20 to about 40 Angstroms.

In another preferred embodiment, X comprises about 6 to about 10 amino acids.

In yet another aspect of the inventive subject matter, the compound binds to a structural motif of the Formula:

MurNAc-Ala-γ-Glu pyrophosphate.

In a more preferred embodiment, the compound which binds to the structural motif has a $K_d$ greater than or equal to about 90 μM.

In another more preferred embodiment, the $K_d$ ranges from about 100 μM to about 3.0 mM.

In addition to the linear form of the compound of the present invention, a cyclic form also has been found. The cyclic form of the inventive compounds is constrained by a lactone that can form between the α-carboxylate of Chp and 3-hydroxyl of β-OH-Asn residues. Further, the inventive compounds can be cyclized to a disulfide between cysteine residues. FIG. 6C depicts one such inventive compound, and as shown in FIGS. 6D and E, the inventive compound is observed to interact with Park's nucleotide. The NMR titration of the inventive compound with Park's nucleotide revealed marked chemical shift changes indicative of complexation.

The cyclic inventive compounds optionally contain about 14 to about 18 amino acids and are expected to take on a cup-shaped conformation comprising beta (β)-strands. We expect that PG intermediates initially bind to the solvent-exposed outer β-strand. However, upon complexation with the intermediates, the inventive compounds undergo a conformational change resulting in the exposure of the hydrophobic core containing hydroxyphenylglycine and phenylalanine creating an exposed hydrophobic face capable of dimerization and oligomerization with other complexes. This ligand-induced exposure of the hydrophobic core is expected to lead to the fibril formation observed in aqueous solution in vitro. The hydrophobic core may be composed of three amino acid residues Chp-Hpg-Phe.

It is expected that fibril formation also occurs at the level of the membrane, and not just in free solution. In the membrane environment, such as that of bacterial cells, the insoluble fibrils are expected to impart beneficial effects, including improved capture of both PG monomers and actively polymerizing PG chains.

As discussed above, it is expected that the inventive compounds anchor to the bacterial cell membrane through their hydrophobic amino acid residues, where they bind to the PG intermediates in the membrane bilayer. Several side chain hydroxyls within each of the inventive compounds assist in the capture of the muramyl carbohydrate of PG precursors. Threonine residues in positions 3 and 6, along with hydroxyphenylglycine residues in positions 4 and 5, of the core "octapeptide" of the inventive compounds play a role in sequestration of the muramyl carbohydrate while the residues in positions 2 and 8 orient and stabilize the ligand in this complex. A surface representation of the residues involved in capture and binding of PG intermediates is shown in FIGS. 6A and B.

The residues at positions 2 and 8 are positively charged due to the cationic charges on their γ-amino groups and are therefore candidates for interacting with the anionic lipid I and II pyrophosphate and/or peptidyl carboxylates and other negatively charged portions of PG intermediate ligands. We expect that the residues in positions 2 and 8 anchor the PG intermediate ligand in the proper orientation for binding using electrostatic or hydrogen bonding interactions. It is expected that preservation of a positive charge on these residues enhance the antibacterial activity of the inventive compounds.

The amino acid residues of the inventive compounds can be further modified in a number of ways, including chlorinations, acylations with cis and/or trans saturated and/or unsaturated fatty acids and glycosylations. Glycosylations can be done with monosaccharides, including mannose, and with disaccharides or polysaccharides. These modifications are expected to stabilize the conformation of the inventive compounds. Stability of the inventive compounds is observed by decreased conformational flexibility and susceptibility to acid hydrolysis. The time-dependent decomposition in acidic solutions of the inventive compounds in non-modified form displayed rapid decomposition in neat trifluoroacetic acid ("TFA") and modest rates of decomposition in 0.1% aqueous TFA and when exposed to solutions containing 1 to 10% hydrochloric acid or acetic acid. However, when the inventive compounds were glycosylated they were resistant to acid hydrolysis over similar time regimes and conditions examined. In effect, these modifications ensure antibiotic integrity in low pH extracellular environments, and protects the present antibacterial compounds from deleterious proteolytic degradation. As a result, by stabilizing and protecting the inventive compounds, these modifications in turn help to improve the antibacterial activity of the inventive compounds.

Treatment Methods of the Present Invention

For many decades antimicrobial chemotherapy has been utilized successfully for the treatment of infectious disease. However, the widespread use of broad spectrum antibiotics has placed enormous selective pressures on bacterial populations, forcing the evolution of resistance mechanisms. Initially, as resistance arose against one class of antibiotics, such as the penicillins, the problem was overcome by the introduction of new classes of antibiotics, such as the aminoglycosides, macrolides, and glycopeptides, as well as the chemical modification of existing drugs. Unfortunately, over the past decade, antibiotic resistance has emerged in virtually all hospital-acquired pathogen-antimicrobial agent combinations.

Since about 5% of all patients admitted to acute care hospitals acquire opportunistic infections, inhibiting bacterial colonization is of paramount importance clinically. Seven leading pathogen groups have accounted for most of the increase in hospital-acquired, or nosocomial) infections in the United States between 1980 and present: *Escherichia coli*, coagulase-negative *Staphylococci*, *Streptococcus*, *Pseudomonas aeruginosa*, *Staphylococcus aureus*, *Enterococcus faecium*, and *Candida albicans*—the majority of which are Gram-positive bacteria. Patients recovering from invasive surgery or burn trauma, or with long-term intravenous lines, intercranial shunts, and indwelling catheters are at high risk for developing opportunistic infections from these organisms. Likewise, individuals immunocompromised due to organ transplantation, HIV-AIDS, or intensive chemotherapy of leukemia, lymphoma, or other neoplastic cancers are vulnerable to nosocomial infection. Antibiotic resistance results in morbidity and mortality from treatment failures and increased health care costs, presently estimated by the National Centers for Disease Control and Prevention to be over $4 billion annually. Given our dwindling arsenal of effective antibiotics, primarily consisting of vancomycin, the drug of last resort for treatment of Gram-positive pathogens, it is not difficult to foresee a time when our most serious infectious threats will be untreatable.

Thus, the present inventive subject matter relates to a method for treating a Gram positive bacterial infection in an animal, which comprises administering to said animal an effective amount of a compound of the present inventive subject matter. Thus, the present inventive subject matter relates to a method for treating a Gram positive bacterial infection in an animal, which comprises administering to said animal an effective amount of a compound of Formula I:

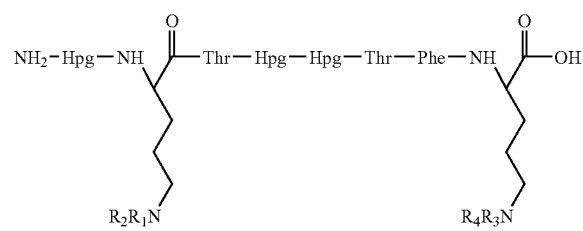

I wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-Me$_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

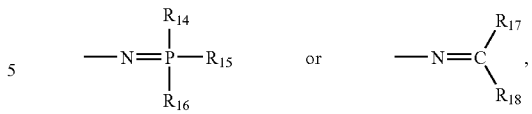

or are taken together with the nitrogen associated with each pair of $R_1$ and $R_2$ and/or $R_3$ and $R_4$, to form a ring in

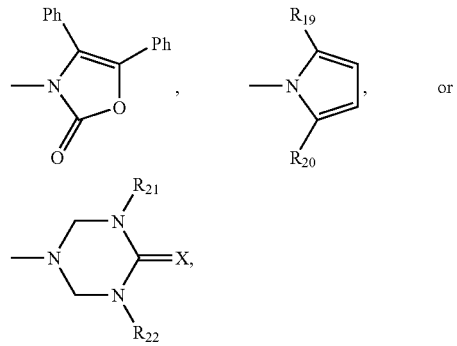

or $R_1$ and $R_2$, $R_3$ and $R_4$, or both $R_1$ and $R_2$, and $R_3$ and $R_4$, are independently replaced by a stable quaternary ammonium salt complex of Formula III:

III and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

n is 1–9;

X is O or S;

Y is F, Cl, Br, or I;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members;

and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl.

In another aspect of the inventive subject matter, $R_1$, $R_2$, $R_3$, and $R_4$ are independently selected from the, group consisting of:

hydrogen, straight or branched chain $C_1$–$C_6$ alkyl, and straight or branched chain $C_1$–$C_6$ alkyl wherein 1 to 3 hydrogen atoms attached to a carbon atom of said alkyl is/are replaced with $NR_5R_6$; and $R_5$ and $R_6$ are independently selected from the group consisting of hydrogen and straight or branched chain $C_1$–$C_6$ alkyl.

In another aspect of the inventive subject matter, the compound is:

H₂N-Hpg-Orn-Thr-Hpg-Hpg-Thr-Phe-Orn-COOH.

In a preferred embodiment, the compound binds to a structural motif of the Formula: MurNAc-Ala-γ-Glu pyrophosphate.

In a more preferred embodiment, the compound which binds to the structural motif has a $K_d$ greater than or equal to about 90 μM.

In another more preferred embodiment, the $K_d$ ranges from about 100 μM to about 3.0 mM.

In a preferred embodiment, said Gram positive bacterial infection is caused by bacteria selected from the group consisting of *Bacillus, Clostridium, Staphylococcus, Streptococcus, Enterococcus, Mycobacterium*, and combinations thereof.

In a more preferred embodiment, the *Bacillus* is selected from the group consisting of *Bacillus anthracis, Bacillus azotoformans, Bacillus cereus, Bacillus coagulans, Bacillus israelensis, Bacillus larvae, Bacillus mycoides, Bacillus polymyxa, Bacillus pumilis, Bacillus stearothormophillus, Bacillus subtilis, Bacillus thuringiensis, Bacillus validus, Bacillus weihenstephanensis*, and *Bacillus pseudomycoides*.

In another more preferred embodiment, the *Clostridium* is selected from the group consisting of *Clostridium aerotolerans, Clostridium aurantibutyricum, Clostridium beijerinckii, Clostridium botulinum A, Clostridium botulinum B, Clostridium botulinum C, Clostridium botulinum D, Clostridium botulinum E, Clostridium botulinum F, Clostridium butyricum, Clostridium chauvoei, Clostridium difficile, Clostridium intestinale, Clostridium novyi A, Clostridium pateurianum, Clostridium saccharolyticum, Clostridiurm septicum, Clostridium thermoaceticum, Clostridium thermosaccharolyticum, Clostridium acetobutylicum, Clostridium bifermenans, Clostridium cadaveris, Clostridium haemolyticum, Clostridium novyi B, Clostridium novyi C, Clostridium perfringens, Clostridium putrefaciens, Clostridium sordelli, Clostridium sporogenes, Clostridium acidiurici, Clostridium irregularis, Clostridium kluyveri, Clostridium oxalicum, Clostridium propionicum, Clostridium sticklandlii, Clostridium villosum, Clostridium argeninense, Clostridium ghoni, Clostridium limosum, Clostridium putrefaciens, Clostridium subterminale*, and *Clostridium tetani*.

In another more preferred embodiment, the *Staphylococcus* is selected from the group consisting of *Staphylococcus aureus, Staphylococcus epidermis*, and *Staphylococcus saprophyticus*.

In a further more preferred embodiment, the *Streptococcus* is selected from the group consisting of *Streptococcus pneumoniae, Streptococcus pyogenes, Streptococcus viridans, Streptococcus agalactiae, Streptococcus alpha, Streptococcus beta*, and *Streptococcus gamma*.

In a further more preferred embodiment, the *Mycobacterium* is selected from the group consisting of *Mycobacterium tuberculosis, Mycobacterium bovis, Mycobacterium africanum*, and *Mycobacterium microti*.

In a most preferred embodiment, the bacteria is *Staphylococcus aureus, Enterococcus faecalis*, or *Enterococcus faecium*.

The present inventive subject matter also relates to a method for treating a Gram positive bacterial infection in an animal, which comprises administering to said animal an effective amount of a compound of Formula II:

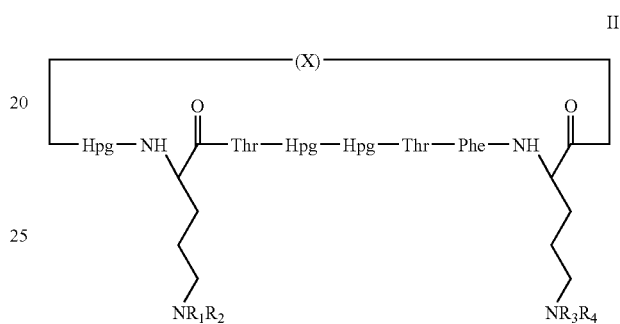

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-Me$_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

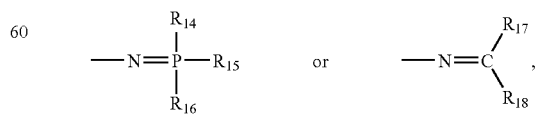

or are taken together with the nitrogen associated with each pair of $R_1$ and $R_2$ and/or $R_3$ and $R_4$, to form a ring in

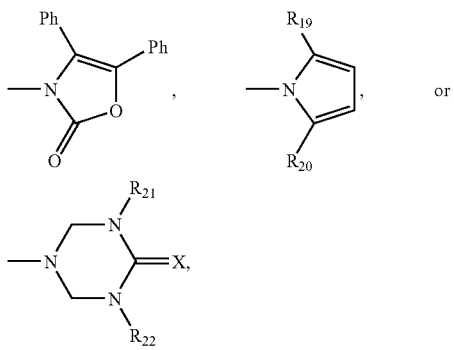

or R$_1$ and R$_2$, R$_3$ and R$_4$/or both R$_1$ and R$_2$, and R$_3$ and R$_4$, are independently replaced by a stable quaternary ammonium salt complex of Formula III:

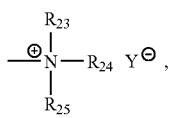

III and wherein R$_8$, R$_{10}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, and R$_{25}$, are independently selected from the group consisting of:
straight or branched C$_1$–C$_9$ alkyl,
straight or branched chain C$_1$–C$_9$ alkyl substituted with one or more halo, trifluoromethyl, nitro, C$_1$–C$_6$ straight or branched chain alkyl, C$_2$–C$_6$ straight or branched chain alkenyl, hydroxy, C$_1$–C$_4$ alkoxy, C$_2$–C$_4$ alkenyloxy, phenoxy, benzyloxy, amino, or Ar,
straight or branched chain C$_2$–C$_9$ alkenyl or alkynyl, and
straight or branched chain C$_2$–C$_9$ alkenyl or alkynyl substituted with one or more halo, trifluoromethyl, nitro, C$_1$–C$_6$ straight or branched chain alkyl, C$_2$–C$_6$ straight or branched chain alkenyl, hydroxy, C$_1$–C$_4$ alkoxy, C$_2$–C$_4$ alkenyloxy, phenoxy, benzyloxy, amino, or Ar;
n is 1–9;
X is O or S;
Y is F, Cl, Br, or I;
Ar is a mono-, bi- or tricyclic, carbo- or heterocyclic ring, wherein the ring is either unsubstituted or substituted in one or more position(s) with halo, hydroxyl, nitro, trifluoromethyl, C$_1$–C$_6$ straight or branched chain alkyl or alkenyl, C$_1$–C$_4$ alkoxy, C$_1$–C$_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and
R$_5$ and R$_6$ are independently selected from the group consisting of hydrogen and straight or branched chain C$_1$–C$_6$ alkyl,
provided that at least one of R$_1$, R$_2$, R$_3$, and R$_4$ is a straight or branched C$_1$–C$_6$ alkyl wherein 1 to 3 hydrogen atoms attached to a carbon atom of said alkyl is/are replaced with NR$_5$R$_6$;
R$_5$ and R$_6$ are independently selected from the group consisting of hydrogen and straight or branched chain C$_1$–C$_6$ alkyl; and
X is a spacer that is less than about 100 Angstroms.
In a preferred embodiment, X is a spacer that is about 20 Angstroms. However, it will understood that X is optionally as small as a direct bond between the Hpg and Orn residues which it bridges.
In a preferred embodiment, R$_1$, R$_2$, R$_3$, and R$_4$ are independently selected from the group consisting of:
hydrogen,
straight or branched chain C$_1$–C$_6$ alkyl, and
straight or branched chain C$_1$–C$_6$ alkyl wherein 1 to 3 hydrogen atoms attached to a carbon atom of said alkyl is/are replaced with NR$_5$R$_6$,
provided that at least one of R$_1$, R$_2$, R$_3$, and R$_4$ is a straight or branched C$_1$–C$_6$ alkyl wherein 1 to 3 hydrogen atoms attached to a carbon atom of said alkyl is/are replaced with NR$_5$R$_6$;
R$_5$ and R$_6$ are independently selected from the group consisting of hydrogen and straight or branched chain C$_1$–C$_6$ alkyl; and
X is a spacer that is less than about 100 Angstroms.
In a preferred embodiment, X is within the range from about 20 to about 40 Angstroms.
In another preferred embodiment, X comprises about 6 to about 10 amino acids.
In yet another aspect of the inventive subject matter, the compound binds to a structural motif of the Formula: MurNAc-Ala-γ-Glu pyrophosphate.
In a more preferred embodiment, the compound which binds to the structural motif has a K$_d$ greater than or equal to about 90 μM.
In a further more preferred embodiment, the K$_d$ ranges from about 100 μM to about 3.0 mM.
In another aspect of the inventive subject matter, said Gram positive bacterial infection is caused by bacteria selected from the group consisting of *Bacillus, Clostridium, Staphylococcus, Streptococcus, Enterococcus, Mycobacterium*, and combinations thereof. As discussed in greater detail above, the compounds of the present invention are effective against a number of *Bacillus, Clostridium, Staphylococcus, Streptococcus,* and *Mycobacterium* species.
In a most preferred embodiment, the bacteria is *Staphylococcus aureus, Enterococcus faecalis,* or *Enterococcus faecium.*
Seven of the amino acids utilized in synthesizing the compounds of the present inventive subject matter must be synthesized. Generation of the unusual 2S,3S stereochemistry of the orthogonally-protected β-hydroxy-L-asparagine residue suggest a transform whereby the stereochemistry at C2 and C3 are established in one step from the regioselective opening of a chiral epoxide. A key transform in the assembly of Chp is a stereoselective Sharpless, asymmetric aminohydroxylation of a styrene precursor, accomplished by functional group transformation of the related benzoic acid. Protected L-Hpg residues are assembled by racemization and chiral resolution of the commercially available D-Hpg isomer. Assembly of the mannose disaccharide is accomplished by way of a Koenigs-Knorr condensation transform as a key step. Disconnection of the C3–C4 σ-bond of the N-terminal C-9 fatty acid and its unusual cis,trans regiochemistry suggest a stereoselective palladium-(0) catalyzed Stille cross-coupling transform.

Synthesis of Component Amino Acids (a) Synthesis and Resin Attachment of L-3-Chloro-4-hydroxyphenylglycine. We prepare Fmoc-L-Chp-(OH)-OAllyl from commercially available 3-chloro-4-hydroxybenzoic acid. As depicted in Scheme XVI, 3-chloro-4-hydroxybenzoic acid compound 3 is converted into the tert-butyl-protected benzylaldehyde compound 4. Subsequent Wittig homologation yields a styrene which is used as a starting substrate for the Sharpless asymmetric aminohydroxylation reaction. tert-Butyl carbamate is employed as the nitrogen source for the asymmetric aminohydroxylation reaction instead of benzyl carbamate to avoid potential ring dechlorination by hydrogenolysis, which is potentially encountered during Cbz removal. Ruthenium tetraoxide, $RuO_4$, oxidation followed by Boc/tert-butyl ether deprotection with trifluoroacetic acid affords 3-chloro-4-hydroxyphenylglycine. Chp is subsequently protected at α-$NH_2$ as the Fmoc group and at α-COOH group as the allyl ester, forming Fmoc-L-Chp-(OH)-OAllyl compound 6.

Compound 6 is attached as the first residue to the solid support in a rather unconventional, yet versatile manner; the unprotected side chain phenolic hydroxyl of 6 is anchored to a trialkylsilylchloride-modified polystyrene resin via a silyl ether σ-bond, yielding conjugate compound 7. This method affords unimpeded peptide chain assembly by Fmoc-SPPS, yet also leaves the α-COOH group free for macrolactonization with OH-Asn2. To our knowledge, this silyl-based side chain phenolic attachment method has not been exploited in peptide synthesis, and thus is a useful addition to the synthesis of linear and cyclic peptides, and combinatorial libraries, where tyrosine or other phenolic residues, such as Chp and Hpg, are found within a sequence.

We derivatize the trialkylsilylchloride resin with Chp under standard silyl ether forming conditions, in polystyrene-$R_3$SiCl and imidazole. A resin-bound TBDMS-Cl equivalent is expected to afford the most stable silyl ether attachment. Resin loading and peptide coupling efficiencies are determined by quantitative ninhydrin analysis. Because

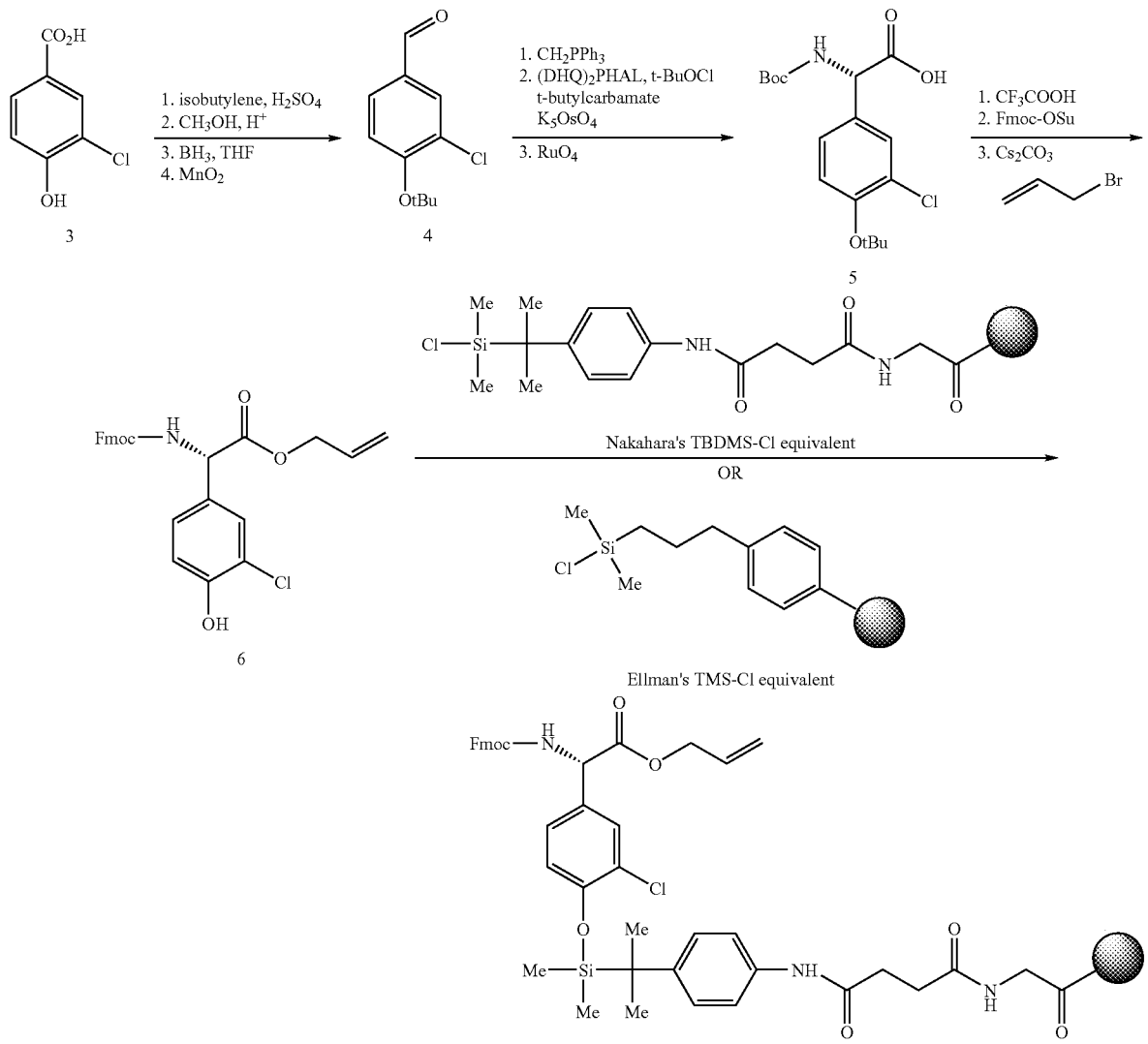

phenolic silyl ethers exhibit markedly different reactivities toward fluoridolysis and acid hydrolysis as compared to their alkyl ether counterparts, conditions for optimal cleavage are tailored to complement the reactivity of the peptide-resin silyl ether bond.

(b) Synthesis of Hydroxyphenylglycine Modules. Protected forms of the D- and L-enantiomers of 4-hydroxyphenylglycine (hereinafter "Hpg") present in the sequence of the inventive compounds are synthesized from a common precursor, commercially available D-Hpg, compound 8. We have created an orthogonal side chain protection scheme for Hpg residues which permits stepwise chain elongation by standard Fmoc/piperidine protocols, yet allow the side chain protecting group to be removed under relatively mild conditions, with fluoridolysis or acid hydrolysis. AS shown in scheme XVII, to synthesize an SPPS module of D-Hpg, we protect the free amine as the Fmoc group with Fmoc-OSu, followed by side chain protection as the tert-butyldimethylsilyl ether with TBDMS-Cl, producing compound 9.

fully used this alternate methodology to synthesize Fmoc-γ-carboxy-L-glutamic acid di-tert-butyl ester (Fmoc-Gla(OtBu)-OH). Likewise, a route to phenylglycines via oxazolidone chiral auxiliaries would provide another means to obtain this class of compounds.

Scheme XVIII

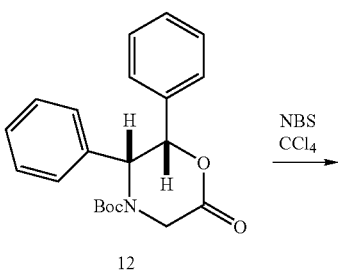

12

SCHEME XVII

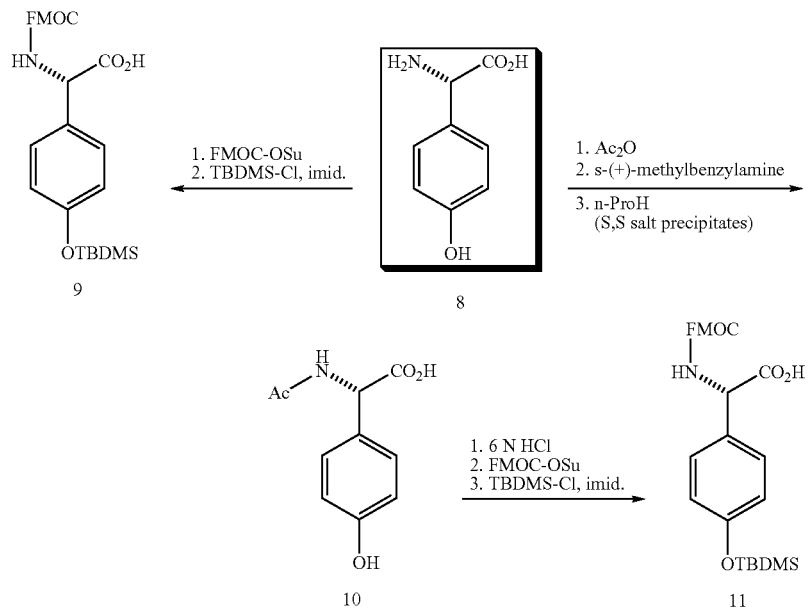

Given the commercial availability and relatively low cost of D-Hpg, we employ a racemization-resolution approach to generate gram quantities of enantiopure L-Hpg with >100 mmol scales. We acetylate D-Hpg with acetic anhydride, then racemize the N-acetylated product by heating in the presence of S-(+)-methylbenzylamine (hereinafter "MBA"). Selective precipitation of compound 10 as the S,S MBA salt, removal of MBA by triethylamine, and finally 6N HCl hydrolysis produces the free amino acid L-Hpg. As in the preceding case for the D-Hpg isomer, a SPPS module is generated from the hydrochloride salt of L-Hpg by sequential Nα-Fmoc and sidechain TBDMS protection. This building block compound 11, and a partially protected form of L-Hpg, are used, for example, for sidechain attachment of a α-D-Man-(1→2)-α-D-Man disaccharide.

In an alternate method for phenylglycine assembly, as shown in Scheme XVIII, enantioselective amino acid syntheses such as chiral oxazinone-directed glycine enolate chemistry is also readily employed to generate D- or L-phenylglycines. Both enantiomers of the oxazinone auxiliary compound 12 are commercially available. We have success- -continued

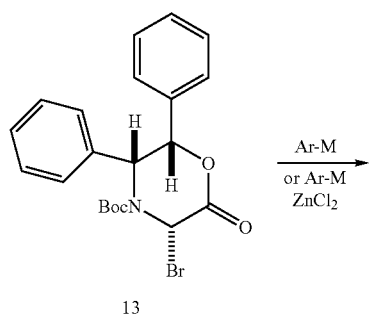

13

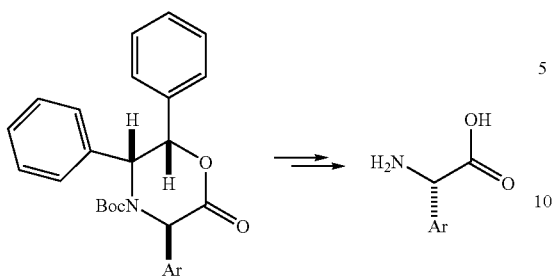

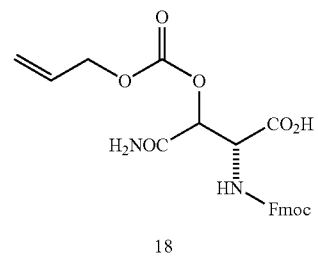

(c) Synthesis of Orthogonally Protected β-OH Hydroxyassaragines. The (2S,3S)-3-hydroxyasparagine residue, three isomer is generated by enantioselective syntheses.

As depicted in Scheme XIX, we synthesize the 2S,3S isomer of 3-hydroxyasparagine, compound 17, from commercially available D-diethyl tartrate, compound 14. Specifically, we convert 14 into chiral epoxide, compound 15, by hydrobromination followed by base-catalyzed epoxidation. Enantioselective ring opening of compound 15 with hydrazoic acid, $HN_3$, affords azidoalcohol, compound 16. Reduction of 16 by regioselective ammonolysis, and selective hydrolysis of the ester with lithium hydroxide, LiOH, provides 3-hydroxyasparagine, compound 17. Subsequent Fmoc protection of the amine followed by sidechain hydroxyl protection as allyl carbonate forms the desired product, (2S,3S)-Fmoc-Asn(OAlloc)-OH, compound 18, to be used directly as a SPPS module. Since this residue has the desired 3S configuration at C-3, lactonization of Chp17 with β-OH Asn is performed using carbodiimide activation to ensure that the stereochemistry of C-3 is preserved.

Alternate methods for β-OH Asn synthesis are available. For example, to generate the core amino alcohol structure, we apply a osmium-catalyzed Sharpless asymmetric aminohydroxylation reaction to C2 symmetric Z-succinates, such as succinic anhydride. Since in the Sharpless asymmetric aminohydroxylation reaction syn addition is anticipated, only one L-, D-pair is predicted, reducing the number of possible stereoisomers from four to two due to the symmetry of the substrate. Once an aminoalcohol core structure is generated, subsequent functional group transformations create the protected β-OH Asn module. Since this reaction sequence would be expected to yield the 2S,3R isomer, the opposite of what is generally found in the inventive compounds, we additionally use Mitsunobu conditions, $Ph_3P$ and DEAD for peptide macrolactonization. Because the Mitsunobu reaction proceeds with inversion of stereochemistry, the 2S,3S isomer is then generated at C-3 as a result of macrolactonization.

(d) Synthesis of the C-9 Fatty Acid (2Z,4E)-7-Methyloctadi-2,4-eneoic acid. An inventive compound is N-terminally acylated with an octanoic acid derivative containing a Z,E diene, compound 26. We expect that this modification facilitates membrane anchoring, since by NMR the inventive compounds tightly associate with unilamellar phospholipid vesicles which mimic cell membranes. We also expect that lipidation facilitates translocation through the Gram-positive bacterial cell membrane. We assemble the Z,E lipid stereoselectively, employing a palladium-catalyzed Stille cross-coupling reaction between the known E-stannane, compound 25, and Z-bromide, compound 22, as depicted in Scheme XX. Both substrates for the Stille coupling are available in one step from commercially available starting materials. Alternatively, more traditional olefination methods are available with the appropriate carbonyl-containing substrates, for example Wittig, Horner-Wadsworth-Emmons, or Peterson approaches.

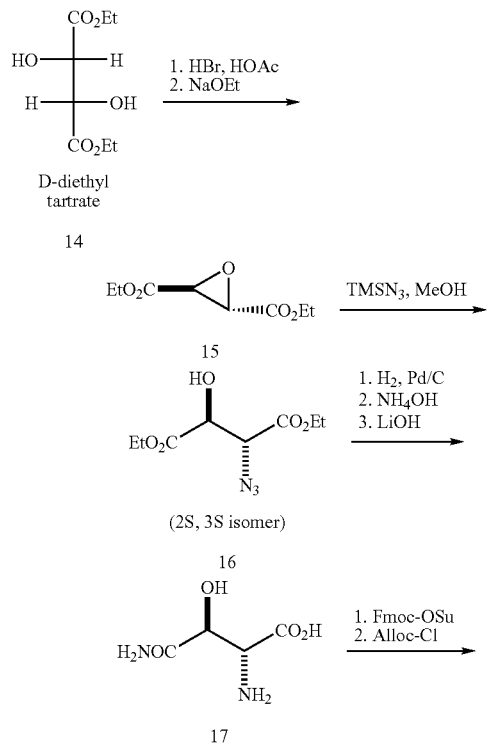

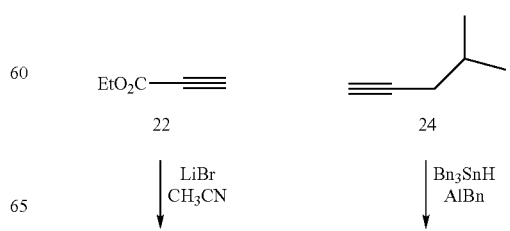

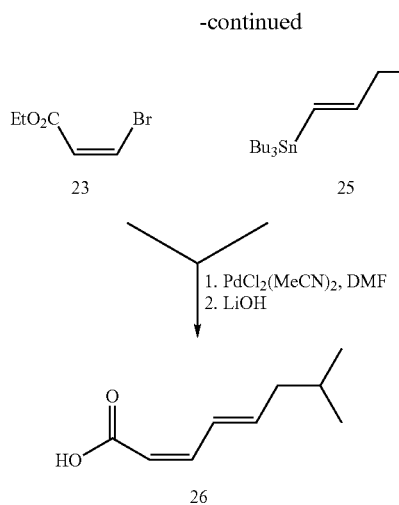

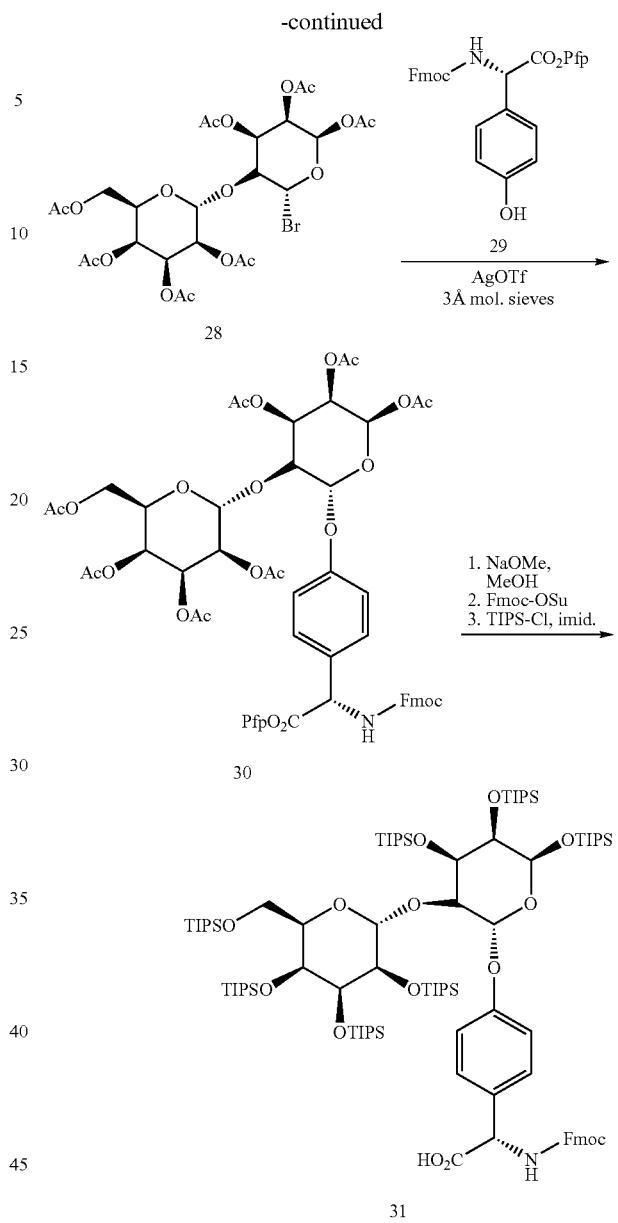

(e) Synthesis of Nα-Fmoc-L-Hpg(α-D-Man-(1→2)-α-D-Man)-OPfo. The inventive compounds contain a pendant α(1→2)-linked mannose disaccharide attached to the side chain hydroxyl of L-Hpg11. Reported antibiotic minimal inhibitory concentration values suggest that the disaccharide has little to no effect on the antibiotic mechanism. Three functional roles are plausible: (1) the sugar plays a role in maintaining solubility; (2) the sugar stabilizes folded conformation, as has been observed for other carbohydrate-modified proteins; or (3) the carbohydrate confers a supplemental secondary antibiotic effect as an inhibitor of glycosyl transfer, such as transglycosylation.

Our method for synthesis of a mannose disaccharide-Hpg glycoconjugate is based on modified Koenigs-Knorr conditions for the efficient coupling of glycosyl bromides, including an α(1→2)-linked mannose disaccharide, to pentafluorophenol esters of Fmoc-tyrosine, Fmoc-serine, Fmoc-threonine, and Fmoc-hydroxyproline. We expect that Hpg should couple well to glycosyl bromides given its structural similarity to tyrosine. We convert penta-O-acetyl-α-D-mannopyranose, compound 27, into the dimannosyl α-bromide, compound 28, as shown in Scheme XXI. Separately, the glycosyl acceptor Fmoc-L-Hpg-OPfp, compound 2:9, is prepared by *carbodiimide-mediated condensation of Fmoc-L-Hpg-OH with pentafluorophenol, Pfp-OH. Subsequent silver triflate-promoted Koenigs-Knorr glycosylation of Na-Fmoc-L-Hpg-OPfp with a-bromide compound 28 provides the fully protected glycoconjugate, compound 30. In the alternate, silyl-based carbohydrate protection methods for removal of carbohydrate peracetate protecting groups, e.g. module 31.

Scheme XXI

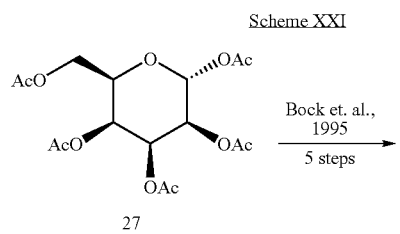

Synthesis of Compounds of the Invention

The compounds of the present invention can be readily prepared by standard chemical synthesis techniques, including standard Fmoc solid-phase peptide synthesis and solution-phase methods as described in detail above for specific amino acids, and as otherwise known to one of ordinary skill in the art.

In the preparation of the compounds of the invention, one skilled in the art will understand that it is necessary to protect or block various reactive functionalities on the starting compounds or intermediates while a desired reaction is carried out on other portions of the molecule. After the desired reactions are complete, or at any desired time, normally such protecting groups are removed by, for example, hydrolytic or hydrogenolytic means. Such protection and deprotection steps are conventional in organic chemistry and are known to ordinarily skilled artisans, who are hereby referred to "Protective Groups in Organic Chemistry," McOmie, ed., Plenum Press, New York, New York; and "Protective Groups in Organic Synthesis," Greene, ed., John Wiley & Sons, New York, N.Y. (1981) for the teaching of additional protective groups which may be useful in the preparation of compounds of the present invention.

The product and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like. Such isolation and purification steps are conventional in organic chemistry and are known to ordinarily skilled artisans.

Route(s) of Administration

The route(s) of administration of the compounds and compositions of the present invention are well known to those skilled in the art (see, for example, "Remington's Pharmaceutical Sciences", 18th Edition, Chapter 86, pp. 1581–1592, Mack Publishing Company, 1990). The compounds and compositions may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

To be effective therapeutically as central nervous system targets, the compounds and compositions should readily penetrate the blood-brain barrier when peripherally administered. Compounds which cannot penetrate the blood-brain barrier can be effectively administered by an intraventricular route.

The compounds and compositions may be administered in the form of sterile injectable preparations, for example, as sterile injectable aqueous or oleaginous suspensions. These suspensions, may be formulated according to techniques known in the art using suitable, dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in another aspect of the inventive subject matter, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule; to further enhance stability and provide release in the intestinal tract to improve absorption, is the best mode of administration currently contemplated.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Further, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the present invention may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bio-erodible particles or beads and depot injections, are also known to those skilled in the art.

Dosage

Dosage levels on the order of about 0.001 mg to about 100 mg per kilogram body weight of the active ingredient compounds or compositions are useful in the treatment of the above conditions, with levels ranging from 200 mg per day to 1600 mg per day. The compounds and compositions of the present invention may usually be given in two or three doses daily. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present invention and are not intended to be limitations thereon. Unless otherwise indicated, all percentages are based upon 100% by weight of the final composition.

Mass spectra were recorded on commercially available spectrometers and HPLC was performed on a commercially available columns. Both the NMR spectroscopy and transmission electron micrographs were performed in a manner known to one of ordinary skill in the art. Fmoc-amino acids and deuterated solvents were purchased from a commercial supplier. Measurement of dissociation constants was performed by NMR.

UDP-MurNAc-L-Ala-γ-D-Glu-L-Dap-D-Ala-D-Ala pentapeptide (Park's nucleotide) and UDP-MurNAc-L-Ala-γ-D-Glu-L-Dap tripeptide were isolated from *Bacillus subtilis* by methods known to those of ordinary skill in the art.

Example 1

Preparation of a Cyclic Antibacterial Compound of the Present Invention

The following example illustrates the preparation of a cyclic antibacterial compound diguanidylated at the ornithine residues provided according to the present invention.

A linear form of the compound containing an octapeptide of the formula: -Hpg-Orn-Thr-Hpg-Hpg-Thr-Phe-Orn- was prepared by standard Fmoc solid-phase peptide synthesis methods. The linear compound was then cyclized to a lactone between two amino acids of the linear compound.

A dry nitrogen-flushed 50 ml round bottom flask was charged with 200 mg of the cyclic compound (0.0783 nmol, 1 eq), 458 mg of 1 H-pyrazole-1-carboxamidine (1.57 nmol, 20 eq), and a Teflon stirbar. The flask was sealed and 372 mg diisopropylethylamine (1.57 nmol, 20 eq)in 2 ml DMF was added by syringe. The solution was allowed to stir for 8 hours, then azeotropically evaporated with toluene under high vacuum three times and dried on high vacuum overnight. Excess starting material was removed by washing the solid with 10 ml absolute ethanol with sonication, followed by filtration. The remaining solid was dissolved in HPLC Buffer A, purified by preparative reversed phase HPLC and lyophilized to produce a white solid (80.2 mg, 38.7% yield).

Recognition and Capture of PG Intermediates

Figure 5:
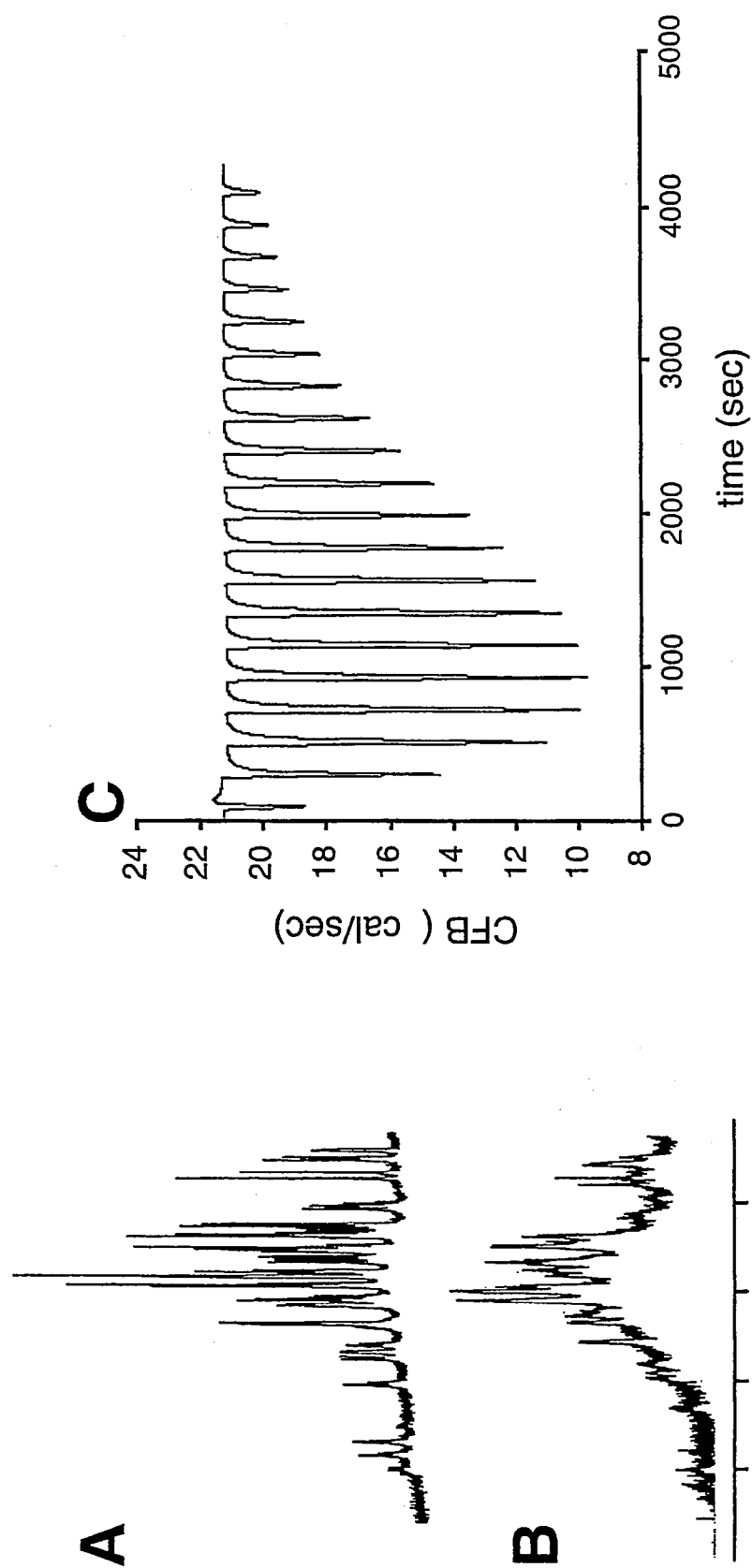
FIG. 5A is a graph which depicts the aromatic and amide region of the $^1$H NMR spectrum of free diguanidylated ornithine residues at positions 2 and 8 of the octapeptide core of a compound of the present invention.
FIG. 5B is a graph which depicts the aromatic and amide region of the $^1$H NMR spectrum of the diguanidylated ornithine residues with, equimolar of Park's nucleotide, depicting the line broadening and chemical shift changes that occur upon binding.
FIG. 5C is a graph which depicts isothermal titration calorimetry data from the titration of the cyclic form of a compound of the present invention diguanidylated at the ornithine residues with Park's nucleotide.

The resultant antibacterial compound was then titrated against a solution of the cytoplasmic PG biosynthetic precursor of lipid II, Park's nucleotide. Isothermal titration calorimetry experiments were used to measure the interaction between the antibacterial compound and Park's nucleotide. The experiments were performed at 25° C. using a titration microcalorimeter equipped with a 250 µL injection syringe and a 400 rpm stirring rate. Both the, antibacterial compound and Park's nucleotide were dissolved in water and vacuum degassed before use. Park's nucleotide (20×10 µL injection of a 5.4 mM solution) was injected into an ITC cell containing ca. 1.3 mL of the antibacterial compound (1 mM). Control experiments were performed under identical conditions by injection of the compound into water alone, Park's nucleotide into water, and the reverse experiment of titrating water into solution of the antibacterial compound or Park's nucleotide. Results from the titration experiments clearly indicated that a ligand-induced aggregation occurred during the titration as depicted in FIGS. 5B and C. The complex pattern of heat released during the titration is indicative of ligand-induced aggregation. Insoluble fibrils were produced from soluble fibril preparations by increasing the ionic strength to greater than or equal to 100 mM. In 20% DMSO, the $K_d$ value of the antibacterial compound with Park's nucleotide was 170±+µM. Further, NMR analysis showed clear evidence of complexation and formation of a large, soluble aggregate. When NMR analysis was conducted for the antibacterial compound with another lipid II precursor, UDP-MurNAc-L-Ala-γ-D-GlU-L-Dap tripeptide, there was also clear evidence of complexation and formation of a large, soluble aggregate.

Example 2

Preparation of a Modified Cyclic Antibacterial Compound of the Present Invention The following example illustrates the preparation of a cyclic antibacterial compound modified at the ornithine residues into secondary amines, provided according to the present invention.

A linear form of the compound containing an octapeptide of the formula: -Hpg-Orn-Thr-Hpg-Hpg-Thr-Phe-Orn- was prepared by standard Fmoc solid-phase peptide synthesis methods. The linear compound was then cyclized to a lactone between two amino acids of the linear compound.

A dry nitrogen-flushed 50 ml round bottom flask was charged with 200 mg of the cyclic compound (0.0783, 1.0 eq), a Teflon stirbar, and sealed. 12 mg Isovaleraldehyde (0.140 mmol, 1.8 eq, 15 µl) in 2 ml DMF was added by syringe and the solution was allowed to stir for 2 hours. The solution was then treated with 15 mg sodium cyanoborohydride (0.234 mmol, 3.0 eq) and stirred for an additional 2.5 hours. The reaction was then quenched with 25 ml 0.1% aqueous TFA, purified by preparative reversed phase HPLC, and lyophilized to give a white solid (31.0 mg, 15%).

Recognition and Capture of PG Intermediates

The resultant antibacterial compound still maintains the side-chain amine cationic charge. Titration experiments of the antibacterial compound with the two lipid II precursors, as in example 1, resulted in a $K_d$ value of 130±20 µM with Park's nucleotide and 1280±140 µM with the other precursor. These values indicate that there was a strong affinity of the antibacterial compound to the two lipid II precursors.

Comparative Example A

Preparation of a Modified Cyclic Compound

The following example illustrates the preparation of a cyclic compound diacetylated at the ornithine residues.

A linear form of the compound containing an octapeptide of the formula: -Hpg-Orn-Thr-Hpg-Hpg-Thr-Phe-Orn- was prepared by standard Fmoc solid-phase peptide synthesis methods. The linear compound was then cyclized to a lactone between two amino acids of the linear compound.

A dry nitrogen-flushed 50 ml round bottom flask was charged with 100 mg of the cyclic compound (0.0392 mmol, 1.0 eq), a Teflon stirbar, and sealed. 6 ml acetonitrile and 5.5 ml DMF were added by syringe and the stirred solution was chilled on an ice bath. 8 mg acetic anhydride (0.0783 mmol, 2.0 eq) and a catalytic amount of pyridine (0.1%) were added, the solution was stirred to 0° C. for 1 hour, and then allowed to warm to room temperature and stirred for 3 hours. The solution was then diluted with aqueous 10 ml TFA (0.1% v/v) and purified by HPLC to give a white solid (11.4 mg, 11%).

Lack of Recognition and Capture of PG Intermediates

The resultant compound lacks the side-chain amine cationic charge. Titration experiments showed an almost 10-fold decrease in binding affinity ($K_d$=1340±320 µM) with Park's nucleotide, exhibiting markedly reduced antibiotic activity. The resultant compound also failed to show detectable binding to UDP-MurNAc-L-Ala-γ-D-Glu-L-Dap tripeptide.

The results in examples 1 and 2 above demonstrate that modifications and variations at positions 2 and 8 of the octapeptide core of the inventive compounds do not inactivate the antibacterial capabilities of the inventive compounds. Therefore, the compound in example 3 above is not within the present inventive subject matter.

Each of the documents referred to in this Specification is hereby incorporated by reference in its entirety.

The invention being thus described, it will be obvious that the same may be modified or varied in many ways. Such modifications and variations are not to be regarded as a departure from the spirit and scope of the invention and all such modifications and variations are intended to be included within the scope of the following claims.

I claim:

1. A compound of Formula I:

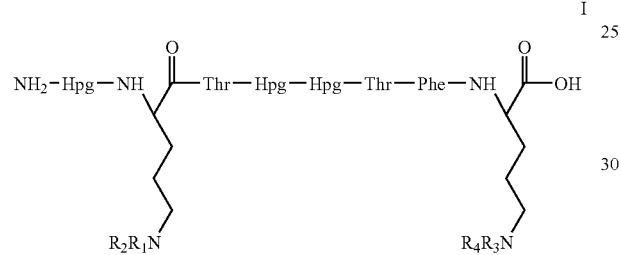

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-$Me_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

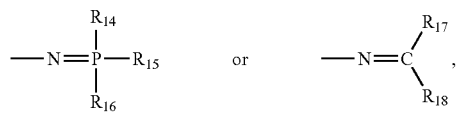

or are taken together with the nitrogen associated with each pair of $R_1$ and $R_2$ and/or $R_3$ and $R_4$, to form a ring in

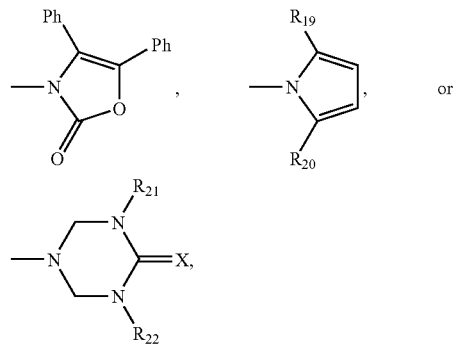

or $R_1$ and $R_2$, $R_3$ and $R_4$, or both $R_1$ and $R_2$, and $R_3$ and $R_4$, are independently replaced by a stable quaternary ammonium salt complex of Formula III:

and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

n is 1–9;

X is O or S;

Y is F, Cl, Br, or I;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl.

2. The compound of claim 1, wherein $R_8$ is selected from the group consisting of fluorenyl, tert-butyl, benzyl, phenyl, and trichloroethyl.

3. The compound of claim 1, wherein:

$R_1$, $R_2$, $R_3$, and $R_4$ are independently selected from the group consisting of:

hydrogen, straight or branched chain $C_1$–$C_6$ alkyl, and straight or branched chain $C_1$–$C_6$ alkyl wherein 1 to 3 hydrogen atoms attached to a carbon atom of said alkyl is/are replaced with $NR_5R_6$; and $R_5$ and $R_6$ are independently selected from the group consisting of hydrogen and straight or branched chain $C_1$–$C_6$ alkyl.

4. The compound of claim 1, wherein the compound is:

H$_2$N-Hpg-Orn-Thr-Hpg-Hpg-Thr-Phe-Orn-COOH.

5. The compound of claim 1, wherein the compound binds to a structural motif of the Formula:

MurNAc-Ala-γ-Glu pyrophosphate.

6. The compound of claim 5, wherein the compound which binds to the structural motif has a $K_d$ greater than or equal to about 90 μM.

7. The compound of claim 6, wherein the $K_d$ ranges from about 100 μM to about 3.0 mM.

8. A compound of Formula II:

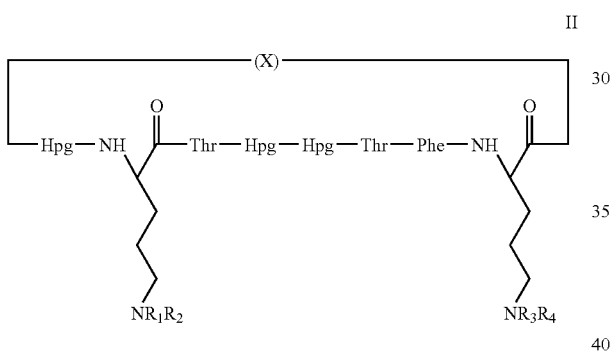

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of CH$_3$C(X)—, CF$_3$C(X)—, CBr$_3$C(X)—, CCl$_3$C(X)—, and CH$_3$(CH$_2$)$_n$C(X)—,

—S(O)(O)—$R_{10}$,

—S—$R_{11}$, wherein $R_{11}$ is selected from the group consisting of C$_6$H$_5$, C$_6$Cl$_5$, C$_6$H$_4$-o-NO$_2$, —S—C$_6$H$_3$-2,4-(NO$_2$)$_2$ AND C(C$_6$H$_5$)$_3$, —P(X)—$R_{12}$, wherein $R_{12}$ is selected from the group consisting of Ph, CH$_3$, PhO, BnO, and iPrO, —C(X)—NH—$R_{13}$, and —(CH$_2$)$_m$—Si-Me$_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

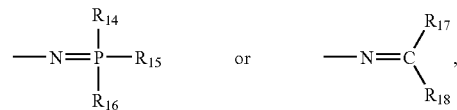

or are taken together with the nitrogen associated with each pair of $R_1$ and $R_2$ and/or $R_3$ and $R_4$, to form a ring in

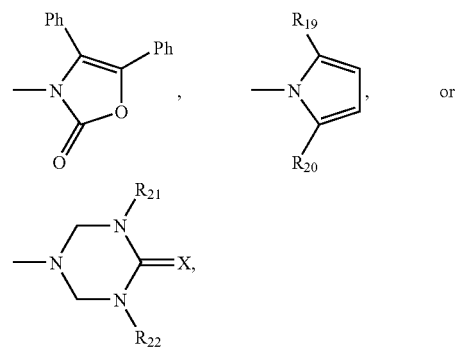

or $R_1$ and $R_2$, $R_3$ and $R_4$, or both $R_1$ and $R_2$, and $R_3$ and $R_4$, are independently replaced by a stable quaternary ammonium salt complex of Formula III:

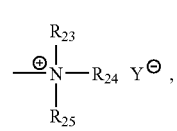

and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

n is 1–9;

X is C or S;

Y is F, Cl, Br, or I;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl, provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;

$R_5$ and $R_6$ are independently selected from the group consisting of hydrogen and straight or branched chain $C_1$–$C_6$ alkyl; and X is a spacer that is less than about 100 Angstroms.

9. The compound of claim 8, wherein X is a spacer that is about 20 Angstroms.

10. The compound of claim 8, wherein $R_8$ is selected from the group consisting of fluorenyl, tert-butyl, benzyl, phenyl, and trichloroethyl.

11. The compound of claim 8, wherein:

$R_1$, $R_2$, $R_3$ and $R_4$ are independently selected from the group consisting of:

hydrogen, straight or branched chain $C_1$–$C_6$ alkyl, straight or branched chain $C_1$–$C_6$ alkyl wherein 1 to 3 hydrogen atoms attached to a carbon atom of said alkyl is/are replaced with $NR_5R_6$, provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;

$R_5$ and $R_6$ are independently selected from the group consisting of hydrogen and straight or branched chain $C_1$–$C_6$ alkyl; and X is a spacer that is at least about 20 Angstroms.

12. The compound of claim 8, wherein X is within the range from about 20 to about 40 Angstroms.

13. The compound of claim 8, wherein X comprises about 6 to about 10 amino acids.

14. The compound of claim 8, wherein the compound binds to a structural motif of the Formula:

MurNAc-Ala-γ-Glu pyrophosphate.

15. The compound of claim 14, wherein the compound which binds to the structural motif has a $K_d$ greater than or equal to about 90 μM.

16. The compound of claim 15, wherein the $K_d$ ranges from about 100 μM to about 3.0 mM.

17. A method for treating a Gram positive bacterial infection in an animal, which comprises administering to said animal an effective amount of a compound of Formula I:

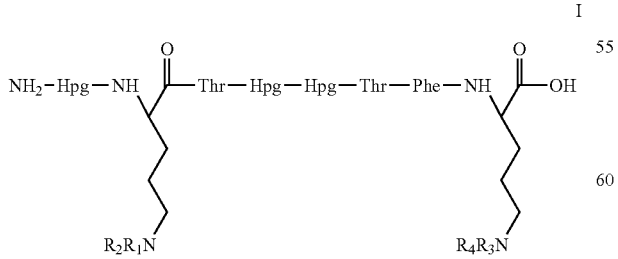

I wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3C(X)$—, $CF_3C(X)$—, $CBr_3C(X)$—, $CCl_3C(X)$—, and $CH_3(CH_2)_nC(X)$—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-Me$_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

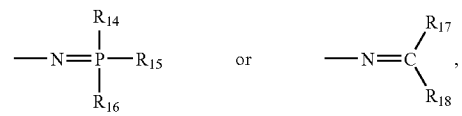

or are taken together with the nitrogen associated with each pair of $R_1$ and $R_2$ and/or $R_3$ and $R_4$, to form a ring in

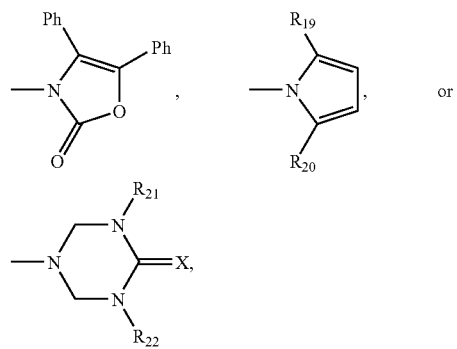

or $R_1$ and $R_2$, $R_3$ and $R_4$, or both $R_1$ and $R_2$, and $R_3$ and $R_4$, are independently replaced by a stable quaternary ammonium salt complex of Formula III:

III and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:

straight or branched $C_1$–$C_9$ alkyl, straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar, straight or branched chain $C_2$–$C_9$ alkenyl or alkynyl, and straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

n is 1–9;

X is O or S;

Y is F, Cl, Br, or I;

Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and $R_5$ and $R_6$ are independently selected from the group consisting of hydrogen and straight or branched chain $C_1$–$C_6$ alkyl.

18. The method of claim 17, wherein $R_8$ is selected from the group consisting of fluorenyl, tert-butyl, benzyl, phenyl, and trichloroethyl.

19. The method of claim 17, wherein: wherein:

$R_1$, $R_2$, $R_3$ and $R_4$ are independently selected from the group consisting of:

hydrogen, straight or branched chain $C_1$–$C_6$ alkyl, and straight or branched chain $C_1$–$C_6$ alkyl wherein 1 to 3 hydrogen atoms attached to a carbon atom of said alkyl is/are replaced with $NR_5R_6$; and $R_5$ and $R_6$ are independently selected from the group consisting of hydrogen and straight or branched chain $C_1$–$C_6$ alkyl.

20. The method of claim 17, wherein the compound is: $H_2$N-Hpg-Orn-Thr-Hpg-Hpg-Thr-Phe-Orn-COOH.

21. The method of claim 17, wherein the compound binds to a structural motif of the Formula:

MurNAc-Ala-γ-Glu pyrophosphate.

22. The method of claim 17, wherein said Gram positive bacterial infection is caused by bacteria selected from the group consisting of *Bacillus, Clostridium, Staphylococcus, Streptococcus, Enterococcus, Mycobacterium*, and combinations thereof.

23. The method of claim 22, wherein the bacteria is *Staphylococcus aureus, Enterococcus faecalis,* or *Enterococcus faecium*.

24. A method for treating a Gram positive bacterial infection in an animal, which comprises administering to said animal an effective amount of a compound of Formula II:

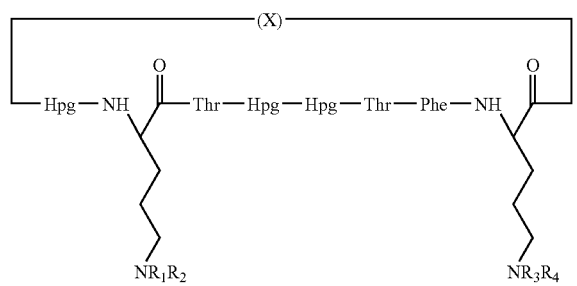

wherein:

$R_1$, $R_2$, $R_3$ and $R_4$ are independently selected from the group consisting of:

hydrogen, straight or branched chain $C_1$–$C_9$ alkyl, straight or branched chain $C_1$–$C_9$ alkyl, wherein 1 to 3 hydrogen atoms attached to a carbon atom of said alkyl is/are replaced with $NR_5R_6$,

—C(O)—O—$R_8$,

—C(O)—$R_9$, wherein $R_9$ is selected from the group consisting of $CH_3$C(X)—, $CF_3$C(X)—, $CBr_3$C(X)—, $CCl_3$C(X)—, and $CH_3(CH_2)_n$C(X)—,

—S(O)(O)—$R_{10}$,

—S—$R_{11}$, wherein $R_{11}$ is selected from the group consisting of $C_6H_5$, $C_6Cl_5$, $C_6H_4$-o-$NO_2$, —S—$C_6H_3$-2,4-$(NO_2)_2$, AND $C(C_6H_5)_3$, —P(X)—$R_{12}$, wherein $R_{12}$ is selected from the group consisting of Ph, $CH_3$, PhO, BnO, and iPrO, —C(X)—NH—$R_{13}$, and —$(CH_2)_m$—Si-Me$_3$, or $R_1$ and $R_2$ are taken together, $R_3$ and $R_4$ are taken together, or both $R_1$ and $R_2$, and $R_3$ and $R_4$, are taken together with the nitrogen associated with each pair of $R_1$ and $R_2$ and/or $R_3$ and $R_4$, to form a double bond in

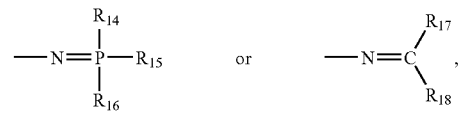

or are taken together with the nitrogen associated with each pair of $R_1$ and $R_2$ and/or $R_3$ and $R_4$, to form a ring in

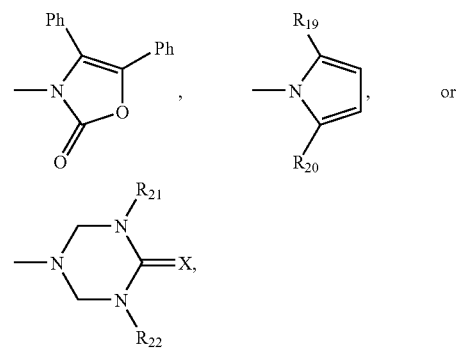

or $R_1$ and $R_2$, $R_3$ and $R_4$, or both $R_1$ and $R_2$, and $R_3$ and $R_4$, are independently replaced by a stable quaternary ammonium salt complex of Formula III:

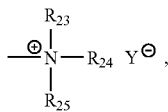

III and wherein $R_8$, $R_{10}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, and $R_{25}$, are independently selected from the group consisting of:
straight or branched $C_1$–$C_9$ alkyl,
straight or branched chain $C_1$–$C_9$ alkyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar,
straight or branched chain $C_2$–$C_9$ alkenyl or alkynyl, and
straight or branched chain $C_2$–$C_9$ alkenyl or alkynyl substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;
n is 1–9;
X is O or S;
Y is F, Cl, Br, or I;
Ar is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S; and
$R_5$ and $R_6$ are independently selected from the group consisting of hydrogen and straight or branched chain $C_1$–$C_6$ alkyl,
provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;
$R_5$ and $R_6$ are independently selected from the group consisting of hydrogen and straight or branched chain $C_1$–$C_6$ alkyl; and
X is a spacer that is less than about 100 Angstroms.

25. The method of claim 24, wherein X is a spacer that is about 20 Angstroms.

26. The method of claim 24, wherein $R_8$ is selected from the group consisting of fluorenyl, tert-butyl, benzyl, phenyl, and trichloroethyl.

27. The method of claim 24, wherein:
$R_1$, $R_2$, $R_3$ and $R_4$ are independently selected from the group consisting of:
hydrogen,
straight or branched chain $C_1$–$C_6$ alkyl,
straight or branched chain $C_1$–$C_6$ alkyl wherein 1 to 3 hydrogen atoms attached to a carbon atom of said alkyl is/are replaced with $NR_5R_6$,
provided that at least one of $R_1$, $R_2$, $R_3$, and $R_4$ is a straight or branched $C_1$–$C_6$ alkyl wherein 1 to 3 hydrogen atoms attached to a carbon atom of said alkyl is/are replaced with $NR_5R_6$;
$R_5$ and $R_6$ are independently selected from the group consisting of hydrogen and straight or branched chain $C_1$–$C_6$ alkyl; and
X is a spacer that is less than about 100 Angstroms.

28. The method of claim 27, wherein X is a spacer that is about 20 Angstroms.

29. The method of claim 24, wherein X is within the range from about 20 to about 40 Angstroms.

30. The method of claim 24, wherein X comprises about 6 to about 10 amino acids.

31. The compound of claim 24, wherein the compound binds to a structural motif of the Formula:

MurNAc-Ala-γ-Glu pyrophosphate.

32. The method of claim 24, wherein said Gram positive bacterial infection is caused by bacteria selected from the group consisting of *Bacillus, Clostridium, Staphylococcus, Streptococcus, Enterococcus, Mycobacterium*, combinations thereof.

33. The method of claim 32, wherein bacteria is *Staphylococcus aureus, Enterococcus faecalis*, or *Enterococcus faecium*.

34. The compound of claim 1, wherein said compound inhibits growth of bacteria.

35. The compound of claim 8, wherein said compound inhibits growth of bacteria.

* * * * *